(12) United States Patent
Nicholas et al.

(10) Patent No.: US 11,633,844 B2
(45) Date of Patent: *Apr. 25, 2023

(54) HAND HELD SURGICAL HANDLE ASSEMBLY, SURGICAL ADAPTERS FOR USE BETWEEN SURGICAL HANDLE ASSEMBLY AND SURGICAL LOADING UNITS, AND METHODS OF USE

(71) Applicant: Covidien LP, Mansfield, MA (US)

(72) Inventors: David A. Nicholas, Trumbull, CT (US); Russell Pribanic, Roxbury, CT (US); John Beardsley, Wallingford, CT (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 320 days.

This patent is subject to a terminal disclaimer.

(21) Appl. No.: 16/869,909

(22) Filed: May 8, 2020

(65) Prior Publication Data

US 2020/0262046 A1 Aug. 20, 2020

Related U.S. Application Data

(63) Continuation of application No. 15/867,914, filed on Jan. 11, 2018, now Pat. No. 10,661,422, which is a
(Continued)

(51) Int. Cl.
*A61B 17/072* (2006.01)
*B25F 3/00* (2006.01)
(Continued)

(52) U.S. Cl.
CPC ............... *B25F 3/00* (2013.01); *A61B 17/00* (2013.01); *A61B 17/07207* (2013.01);
(Continued)

(58) Field of Classification Search
CPC . B25F 3/00; A61B 90/98; A61B 17/00; A61B 17/07207; A61B 2017/00345;
(Continued)

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

AU 2008229795 A1 4/2009
CA 2451558 A1 1/2003
(Continued)

OTHER PUBLICATIONS

Extended European Search Report corresponding to International Application No. EP 15 18 8539.9 dated Feb. 17, 2016.
(Continued)

*Primary Examiner* — Nathaniel C Chukwurah
*Assistant Examiner* — Lucas E. A. Palmer
(74) *Attorney, Agent, or Firm* — Carter, DeLuca & Farrell LLP

(57) ABSTRACT

A surgical device includes an adapter assembly that selectively interconnects a loading unit and a device housing. The adapter assembly includes a drive converter assembly for interconnecting a rotatable drive shaft and an axially translatable drive member of the loading unit. The drive converter assembly converts and transmits a rotation of the rotatable drive shaft to an axial translation of the axially translatable drive member of the loading unit. The drive converter assembly includes a drive element, a drive nut, and a distal drive member. The drive element defines a longitudinal axis. The drive nut is disposed about the longitudinal axis, and the distal drive member is disposed along the longitudinal axis.

20 Claims, 19 Drawing Sheets

Related U.S. Application Data continuation of application No. 13/887,402, filed on May 6, 2013, now Pat. No. 9,868,198.

(60) Provisional application No. 61/654,206, filed on Jun. 1, 2012.

(51) Int. Cl.
*A61B 90/98* (2016.01)
*A61B 17/00* (2006.01)
A61B 90/00 (2016.01)
A61B 17/29 (2006.01)

(52) U.S. Cl.
CPC ...... *A61B 90/98* (2016.02); *A61B 2017/0046* (2013.01); *A61B 2017/00345* (2013.01); *A61B 2017/00367* (2013.01); *A61B 2017/00398* (2013.01); *A61B 2017/00464* (2013.01); *A61B 2017/00473* (2013.01); *A61B 2017/00477* (2013.01); *A61B 2017/00486* (2013.01); *A61B 2017/00734* (2013.01); *A61B 2017/2902* (2013.01); *A61B 2090/0803* (2016.02); *Y10T 279/3412* (2015.01)

(58) Field of Classification Search
CPC ........... A61B 2017/00398; A61B 2017/00473; A61B 2017/00477; A61B 2017/00734
See application file for complete search history.

(56) References Cited

U.S. PATENT DOCUMENTS

| | | | |
|---|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,818,157 A | 4/1989 | Kouvelis |
| 4,823,807 A | 4/1989 | Russell et al. |
| 4,872,456 A | 10/1989 | Hasson |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,170,545 A | 12/1992 | Hubscher |
| 5,224,803 A | 7/1993 | Lallier |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,397,046 A | 3/1995 | Savage et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 * | 12/2003 | Stoddard ............ A61F 9/00745 29/527.4 |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |

(56) References Cited

U.S. PATENT DOCUMENTS

| | | |
|---|---|---|
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Drtiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 * | 9/2010 | Moore ............ A61B 17/07207 227/176.1 |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,874,378 B2 * | 1/2011 | Chen ............... B25D 11/104 173/217 |
| 7,905,897 B2 | 3/2011 | Whitman et al. |
| 7,918,230 B2 * | 4/2011 | Whitman ......... A61B 17/07207 227/19 |
| 7,922,061 B2 | 4/2011 | Shelton, IV et al. |
| 7,922,063 B2 * | 4/2011 | Zemlok ........... A61B 17/00234 227/176.1 |
| 7,922,719 B2 | 4/2011 | Ralph et al. |
| 7,947,034 B2 * | 5/2011 | Whitman ............ A61B 17/068 606/1 |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 * | 9/2011 | Whitman ............ A61B 17/115 227/155 |
| 8,035,487 B2 | 10/2011 | Malackowski |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 * | 7/2012 | Hsu ..................... B25F 3/00 81/184 |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,322,455 B2 * | 12/2012 | Shelton, IV ......... A61B 17/105 227/19 |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,394 B2 | 2/2013 | Grand |
| 8,371,492 B2 | 2/2013 | Aranyi et al. |
| 8,372,057 B2 | 2/2013 | Gude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,584,919 B2 | 11/2013 | Hueil et al. |
| 8,623,000 B2 | 1/2014 | Humayun et al. |
| 8,632,463 B2 | 1/2014 | Drinan et al. |
| 8,640,786 B2 | 2/2014 | Aldrich et al. |
| 8,647,258 B2 | 2/2014 | Aranyi et al. |
| 8,657,174 B2 | 2/2014 | Yates et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 * | 3/2015 | Zemlok ............ A61B 17/07207 606/1 |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,574,644 B2 | 2/2017 | Parihar |
| 9,597,104 B2 | 3/2017 | Nicholas et al. |

(56) References Cited

U.S. PATENT DOCUMENTS

| | | | |
|---|---|---|---|
| 9,868,198 B2 | 1/2018 | Nicholas et al. | |
| 10,661,422 B2 | 5/2020 | Nicholas et al. | |
| 2001/0027601 A1 | 10/2001 | Stoddard et al. | |
| 2002/0049454 A1* | 4/2002 | Whitman | A61B 17/00 606/139 |
| 2002/0165541 A1 | 11/2002 | Whitman | |
| 2003/0038938 A1 | 2/2003 | Jung et al. | |
| 2003/0165794 A1 | 9/2003 | Matoba | |
| 2004/0111012 A1 | 6/2004 | Whitman | |
| 2004/0133189 A1 | 7/2004 | Sakurai | |
| 2004/0176751 A1 | 9/2004 | Weitzner et al. | |
| 2004/0230223 A1 | 11/2004 | Bonutti et al. | |
| 2005/0125027 A1 | 6/2005 | Knodel et al. | |
| 2005/0131442 A1 | 6/2005 | Yachia et al. | |
| 2006/0142656 A1 | 6/2006 | Malackowski et al. | |
| 2006/0142740 A1 | 6/2006 | Sherman et al. | |
| 2006/0278680 A1 | 12/2006 | Viola et al. | |
| 2007/0023476 A1 | 2/2007 | Whitman et al. | |
| 2007/0023477 A1 | 2/2007 | Whitman et al. | |
| 2007/0029363 A1 | 2/2007 | Popov | |
| 2007/0055219 A1* | 3/2007 | Whitman | A61B 17/1285 606/1 |
| 2007/0084897 A1 | 4/2007 | Shelton et al. | |
| 2007/0102472 A1 | 5/2007 | Shelton | |
| 2007/0152014 A1 | 7/2007 | Gillum et al. | |
| 2007/0175949 A1 | 8/2007 | Shelton et al. | |
| 2007/0175950 A1 | 8/2007 | Shelton et al. | |
| 2007/0175951 A1 | 8/2007 | Shelton et al. | |
| 2007/0175955 A1 | 8/2007 | Shelton et al. | |
| 2007/0175961 A1 | 8/2007 | Shelton et al. | |
| 2007/0290458 A1 | 12/2007 | Chuang | |
| 2007/0295780 A1 | 12/2007 | Shelton et al. | |
| 2007/0296286 A1 | 12/2007 | Avenell | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0058801 A1 | 3/2008 | Taylor et al. | |
| 2008/0109012 A1 | 5/2008 | Falco et al. | |
| 2008/0110958 A1 | 5/2008 | McKenna et al. | |
| 2008/0167736 A1 | 7/2008 | Swayze et al. | |
| 2008/0185419 A1 | 8/2008 | Smith et al. | |
| 2008/0188841 A1 | 8/2008 | Tomasello et al. | |
| 2008/0197167 A1 | 8/2008 | Viola et al. | |
| 2008/0208195 A1 | 8/2008 | Shores et al. | |
| 2008/0214097 A1 | 9/2008 | Kao | |
| 2008/0237296 A1 | 10/2008 | Boudreaux et al. | |
| 2008/0250570 A1 | 10/2008 | Dayton et al. | |
| 2008/0251561 A1 | 10/2008 | Eades et al. | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2008/0308603 A1 | 12/2008 | Shelton et al. | |
| 2009/0090763 A1* | 4/2009 | Zemlok | A61B 17/07207 227/175.2 |
| 2009/0099876 A1 | 4/2009 | Whitman | |
| 2009/0101692 A1* | 4/2009 | Whitman | A61B 17/072 227/175.1 |
| 2009/0108048 A1 | 4/2009 | Zemlok et al. | |
| 2009/0138006 A1 | 5/2009 | Bales et al. | |
| 2009/0171147 A1 | 7/2009 | Lee et al. | |
| 2009/0182193 A1 | 7/2009 | Whitman et al. | |
| 2009/0194954 A1 | 8/2009 | Hsu | |
| 2009/0206131 A1 | 8/2009 | Weisenburgh, II et al. | |
| 2009/0209990 A1 | 8/2009 | Yates et al. | |
| 2009/0254094 A1 | 10/2009 | Knapp et al. | |
| 2010/0030029 A1 | 2/2010 | Markham | |
| 2010/0044063 A1 | 2/2010 | Chen | |
| 2010/0069942 A1 | 3/2010 | Shelton, IV | |
| 2010/0076460 A1 | 3/2010 | Taylor et al. | |
| 2010/0193568 A1 | 8/2010 | Scheib et al. | |
| 2010/0200636 A1 | 8/2010 | Zemlok et al. | |
| 2010/0211053 A1 | 8/2010 | Ross et al. | |
| 2010/0225073 A1 | 9/2010 | Porter et al. | |
| 2011/0006101 A1 | 1/2011 | Hall et al. | |
| 2011/0017801 A1 | 1/2011 | Zemlok et al. | |
| 2011/0071508 A1 | 3/2011 | Duval et al. | |
| 2011/0077673 A1 | 3/2011 | Grubac et al. | |
| 2011/0079967 A1 | 4/2011 | Presley | |
| 2011/0121049 A1* | 5/2011 | Malinouskas | A61B 90/98 606/1 |
| 2011/0125138 A1* | 5/2011 | Malinouskas | A61B 90/90 606/1 |
| 2011/0132964 A1* | 6/2011 | Weisenburgh, II | A61B 17/3205 227/176.1 |
| 2011/0139851 A1 | 6/2011 | McCuen | |
| 2011/0155783 A1 | 6/2011 | Rajappa et al. | |
| 2011/0155786 A1 | 6/2011 | Shelton, IV | |
| 2011/0172648 A1 | 7/2011 | Jeong | |
| 2011/0174099 A1* | 7/2011 | Ross | A61B 17/115 74/89.32 |
| 2011/0197719 A1 | 8/2011 | Neitzell et al. | |
| 2011/0204119 A1 | 8/2011 | McCuen | |
| 2011/0218522 A1 | 9/2011 | Whitman | |
| 2011/0253765 A1 | 10/2011 | Nicholas et al. | |
| 2011/0255968 A1 | 10/2011 | Boudreau et al. | |
| 2011/0276057 A1 | 11/2011 | Conlon et al. | |
| 2011/0290854 A1* | 12/2011 | Timm | A61B 17/07207 227/178.1 |
| 2011/0295242 A1 | 12/2011 | Spivey et al. | |
| 2011/0295269 A1* | 12/2011 | Swensgard | A61B 34/70 606/130 |
| 2011/0308021 A1 | 12/2011 | Yang et al. | |
| 2012/0000962 A1 | 1/2012 | Racenet et al. | |
| 2012/0024930 A1 | 2/2012 | Myburgh et al. | |
| 2012/0074199 A1 | 3/2012 | Olson et al. | |
| 2012/0089131 A1 | 4/2012 | Zemlok et al. | |
| 2012/0090863 A1 | 4/2012 | Puzio et al. | |
| 2012/0104071 A1 | 5/2012 | Bryant | |
| 2012/0116368 A1 | 5/2012 | Viola | |
| 2012/0143002 A1 | 6/2012 | Aranyi et al. | |
| 2012/0172924 A1 | 7/2012 | Allen, IV | |
| 2012/0223121 A1 | 9/2012 | Viola et al. | |
| 2012/0245428 A1 | 9/2012 | Smith et al. | |
| 2012/0253329 A1 | 10/2012 | Zemlok et al. | |
| 2012/0266709 A1 | 10/2012 | Wang | |
| 2012/0310220 A1 | 12/2012 | Malkowski et al. | |
| 2012/0323226 A1 | 12/2012 | Chowaniec et al. | |
| 2012/0330285 A1 | 12/2012 | Hartoumbekis et al. | |
| 2013/0018361 A1 | 1/2013 | Bryant | |
| 2013/0020106 A1 | 1/2013 | Kuehne et al. | |
| 2013/0093149 A1 | 4/2013 | Saur et al. | |
| 2013/0098966 A1 | 4/2013 | Kostrzewski et al. | |
| 2013/0098968 A1 | 4/2013 | Aranyi et al. | |
| 2013/0098969 A1 | 4/2013 | Scirica et al. | |
| 2013/0181035 A1 | 7/2013 | Milliman | |
| 2013/0184704 A1 | 7/2013 | Beardsley et al. | |
| 2013/0214025 A1 | 8/2013 | Zemlok et al. | |
| 2013/0240596 A1 | 9/2013 | Whitman | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2013/0324978 A1 | 12/2013 | Nicholas et al. | |
| 2013/0324979 A1 | 12/2013 | Nicholas et al. | |
| 2014/0012236 A1 | 1/2014 | Williams et al. | |
| 2014/0012289 A1 | 1/2014 | Snow et al. | |
| 2014/0110455 A1 | 4/2014 | Ingmanson et al. | |
| 2014/0207125 A1 | 7/2014 | Applegate et al. | |
| 2014/0207182 A1 | 7/2014 | Zergiebel et al. | |
| 2014/0236173 A1 | 8/2014 | Scirica et al. | |
| 2014/0236174 A1 | 8/2014 | Williams et al. | |
| 2014/0260505 A1 | 9/2014 | Bowles et al. | |
| 2014/0276932 A1 | 9/2014 | Williams et al. | |
| 2014/0299647 A1 | 10/2014 | Scirica et al. | |
| 2014/0303668 A1 | 10/2014 | Nicholas et al. | |
| 2014/0358129 A1 | 12/2014 | Zergiebel et al. | |
| 2014/0361068 A1 | 12/2014 | Aranyi et al. | |
| 2014/0373652 A1 | 12/2014 | Zergiebel et al. | |
| 2015/0041166 A1 | 2/2015 | Van Der Linde et al. | |
| 2015/0048144 A1 | 2/2015 | Whitman | |
| 2015/0076205 A1 | 3/2015 | Zergiebel | |

(56) References Cited

U.S. PATENT DOCUMENTS

| | | |
|---|---|---|
| 2015/0080912 A1 | 3/2015 | Sapre |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 101856251 A | 10/2010 |
| CN | 102247182 A | 11/2011 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1759652 A2 | 3/2007 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1943958 A1 | 7/2008 |
| EP | 1943976 A2 | 7/2008 |
| EP | 1952769 A2 | 8/2008 |
| EP | 2005898 A2 | 12/2008 |
| EP | 2027819 A1 | 2/2009 |
| EP | 2044890 A1 | 4/2009 |
| EP | 2055243 A2 | 5/2009 |
| EP | 2090247 A1 | 8/2009 |
| EP | 2098170 A2 | 9/2009 |
| EP | 2100561 A2 | 9/2009 |
| EP | 2100562 A2 | 9/2009 |
| EP | 2165664 A2 | 3/2010 |
| EP | 2236098 A2 | 10/2010 |
| EP | 2245994 A1 | 11/2010 |
| EP | 2263568 A2 | 12/2010 |
| EP | 2272443 A1 | 1/2011 |
| EP | 2316345 A1 | 5/2011 |
| EP | 2324776 A2 | 5/2011 |
| EP | 2329773 A1 | 6/2011 |
| EP | 2333509 A1 | 6/2011 |
| EP | 2377472 A1 | 10/2011 |
| EP | 2383071 A1 | 11/2011 |
| EP | 2462878 A1 | 6/2012 |
| EP | 2462880 B1 | 6/2012 |
| EP | 2491872 A1 | 8/2012 |
| EP | 2586382 A2 | 5/2013 |
| EP | 2606834 A2 | 6/2013 |
| EP | 2668910 A2 | 12/2013 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08038488 | 2/1996 |
| JP | 2005125075 A | 5/2005 |
| KR | 20120022521 A | 3/2012 |
| WO | 9503001 A1 | 2/1995 |
| WO | 9915086 A1 | 4/1999 |
| WO | 0072760 A1 | 12/2000 |
| WO | 0072765 A1 | 12/2000 |
| WO | 03000138 A2 | 1/2003 |
| WO | 03026511 A1 | 4/2003 |
| WO | 03030743 A2 | 4/2003 |
| WO | 03065916 A1 | 8/2003 |
| WO | 03077769 A1 | 9/2003 |
| WO | 03090630 A2 | 11/2003 |
| WO | 2004107989 A1 | 12/2004 |
| WO | 2006042210 A2 | 4/2006 |
| WO | 2007016290 A2 | 2/2007 |
| WO | 2007026354 A1 | 3/2007 |
| WO | 2007137304 A2 | 11/2007 |
| WO | 2007145825 A2 | 12/2007 |
| WO | 2008131362 A2 | 10/2008 |
| WO | 2008133956 A2 | 11/2008 |
| WO | 2009039506 A1 | 3/2009 |
| WO | 2007014355 A3 | 4/2009 |
| WO | 2009132359 A2 | 10/2009 |
| WO | 2009143092 A1 | 11/2009 |
| WO | 2009149234 A1 | 12/2009 |
| WO | 2011108840 A2 | 9/2011 |
| WO | 2012040984 A1 | 4/2012 |

OTHER PUBLICATIONS

Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
EP Examination Report issued in Appl. No. EP 13169998.5 dated Jun. 19, 2017.
Australian Examination Report No. 1 corresponding to International Application No. AU 2013205872 dated Oct. 19, 2016.
Japanese Office Action, and English language translation, issued in Appl. No. JP 2013-112657 dated Mar. 30, 2017.
European Search Report dated Jun. 4, 2019, issued in EP Appln. No. 19158268.
Canadian Office Action and Examination Search Report dated Apr. 3, 2019, corresponding to counterpart Canadian Application No. 2,816,233; 4 pages.
International Search Report corresponding to PCT/US2005/027266, completed May 30, 2008 and dated Jun. 18, 2008 (2 pp.).
Extended European Search Report corresponding to EP 08 25 3184.9, completed Feb. 12, 2009 and dated Feb. 27, 2009; (3 pp.).
Extended European Search Report corresponding to EP 10 25 0228.3, completed May 20, 2010 and dated Jun. 1, 2010; (6 pp.).
Extended European Search Report corresponding to EP 10 25 2037.6, completed Mar. 1, 2011 and dated Mar. 9, 2011; (3 pp.).
Extended European Search Report corresponding to EP 10 25 1968.3, completed on Jul. 4, 2011 and dated Jul. 14, 2011; (12 pp.).
Extended European Search Report corresponding to EP 11 15 2266.0, completed Jul. 15, 2011 and dated Jul. 28, 2011; (3 pp.).
Extended European Search Report corresponding to EP 11 25 0462.6, completed Jul. 20, 2011 and dated Jul. 28, 2011; (6 pp.).
Extended European Search Report corresponding to EP 11 25 0771.0, completed Feb. 7, 2012 and dated Feb. 17, 2012; (3 pp.).
Extended European Search Report corresponding to EP 06 78 8914.7, completed May 3, 2012 and dated May 11, 2012; (8 pp.).
Partial European Search Report corresponding to EP 12 18 6177.7, completed Jan. 30, 2013 and dated Feb. 12, 2013; (6 pp.).
Extended European Search Report corresponding to EP No. 11 17 8021.9, dated Jun. 4, 2013; (3 pp).
Extended European Search Report corresponding to EP No. 13 16 3033.7, completed Jun. 27, 2013 and dated Jul. 15, 2013; (8 pp).

(56) References Cited

OTHER PUBLICATIONS

Extended European Search Report corresponding to EP No. 12 18 6177.7, completed Aug. 14, 2013 and dated Aug. 23, 2013; (8 pp).
Partial European Search Report corresponding to EP No. 13 17 1742.3, completed Sep. 17, 2013 and dated Sep. 25, 2013; (8 pp).
Partial European Search Report corresponding to EP No. 13 17 2400.7, completed Sep. 18, 2013 and dated Oct. 1, 2013; (7 pp).
Extended European Search Report corresponding to EP No. 13 17 5475.6, completed Sep. 23, 2013 and dated Oct. 1, 2013; (8 pp).
Extended European Search Report corresponding to EP No. 13 17 5478.0, completed Sep. 24, 2013 and dated Oct. 2, 2013; (6 pp).
Extended European Search Report corresponding to EP No. 13 17 5479.8, completed Sep. 27, 2013 and dated Oct. 10, 2013; (7 pp).
Partial Extended European Search Report corresponding to EP 13 17 5477.2, completed Oct. 7, 2013 and dated Oct. 15, 2013; (7 pp).
Extended European Search Report corresponding to EP No. 08 25 2703.7, completed Oct. 23, 2008 and dated Oct. 31, 2008; (7 pp).
European search Report from Appl. No. 13177163.6 dated Nov. 15, 2013. (8 pp).
Extended European Search Report from EP Application No. 13172400.7 dated Jan. 21, 2014.
Extended European Search Report from EP Application No. 13189026.1 dated Jan. 31, 2014.
Extended European Search Report from Application No. EP 13177163.6 dated Feb. 6, 2014.
Extended European Search Report from Application No. EP 13175477.2 dated Feb. 6, 2014.
Extended European Search Report corresponding to EP 13176805.3, dated Nov. 4, 2013.
Extended European Search Report from Application No. EP 13171742.3 dated Jan. 3, 2014.
Extended European Search Report from Application No. EP 13169998.5 dated Feb. 24, 2014.
Chinese Office Action dated May 5, 2016 for application No. 2013102174450.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 79702 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.

\* cited by examiner

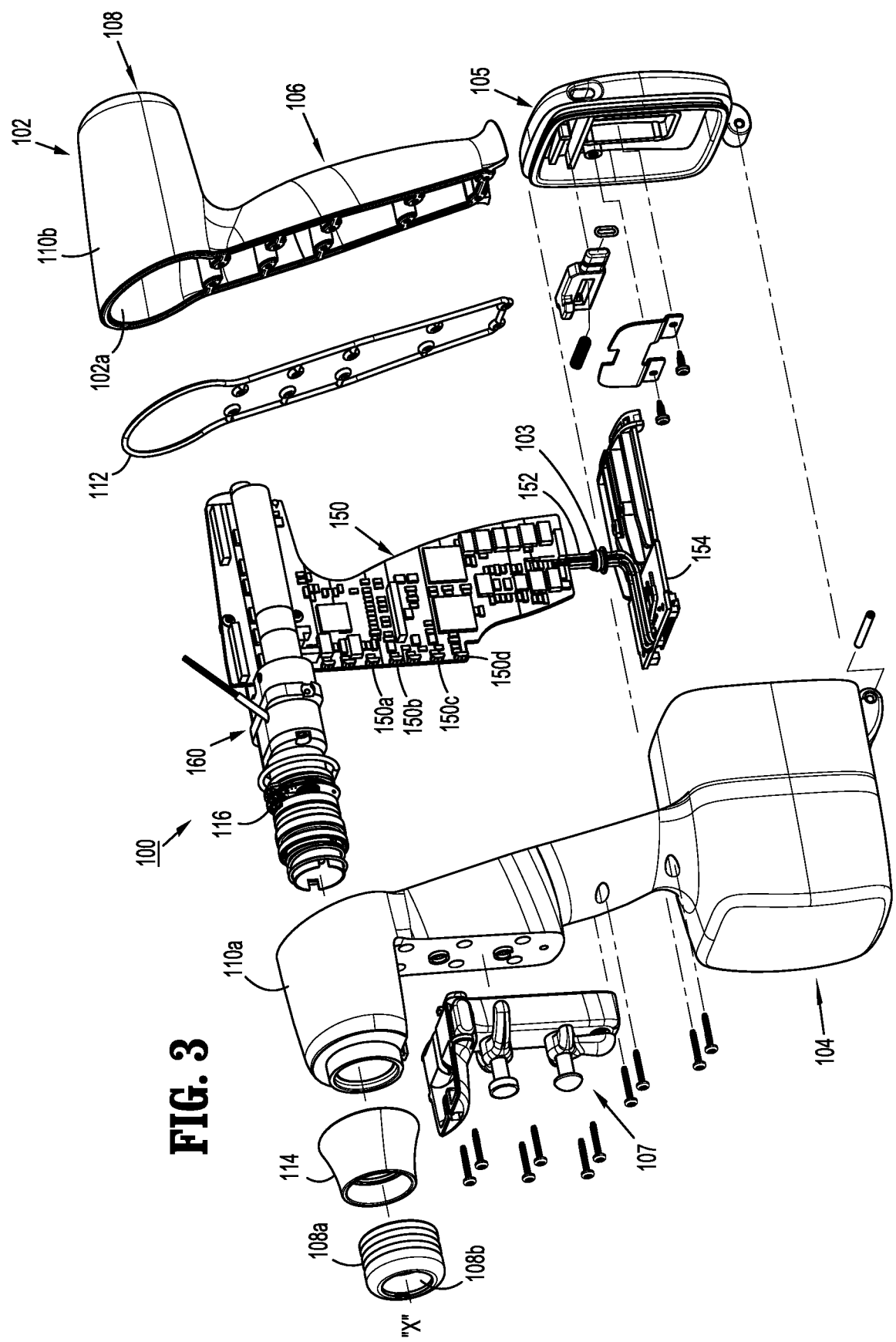

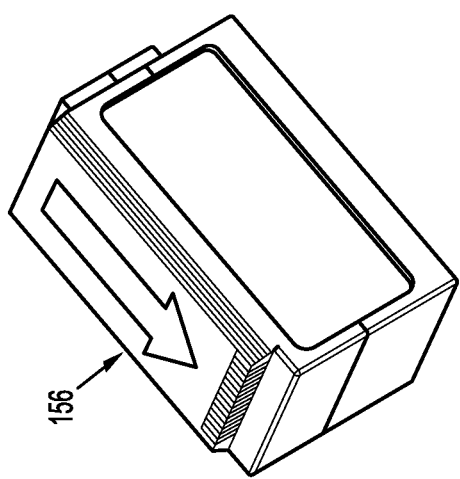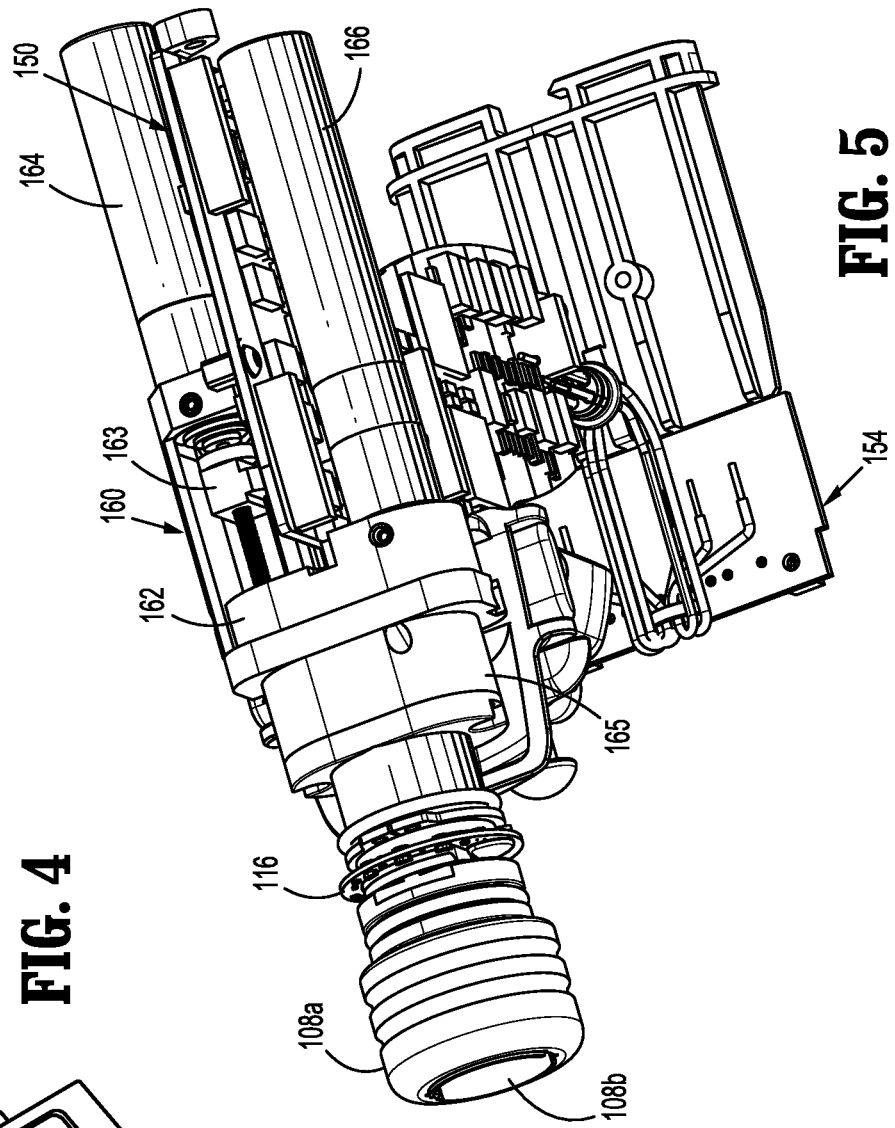

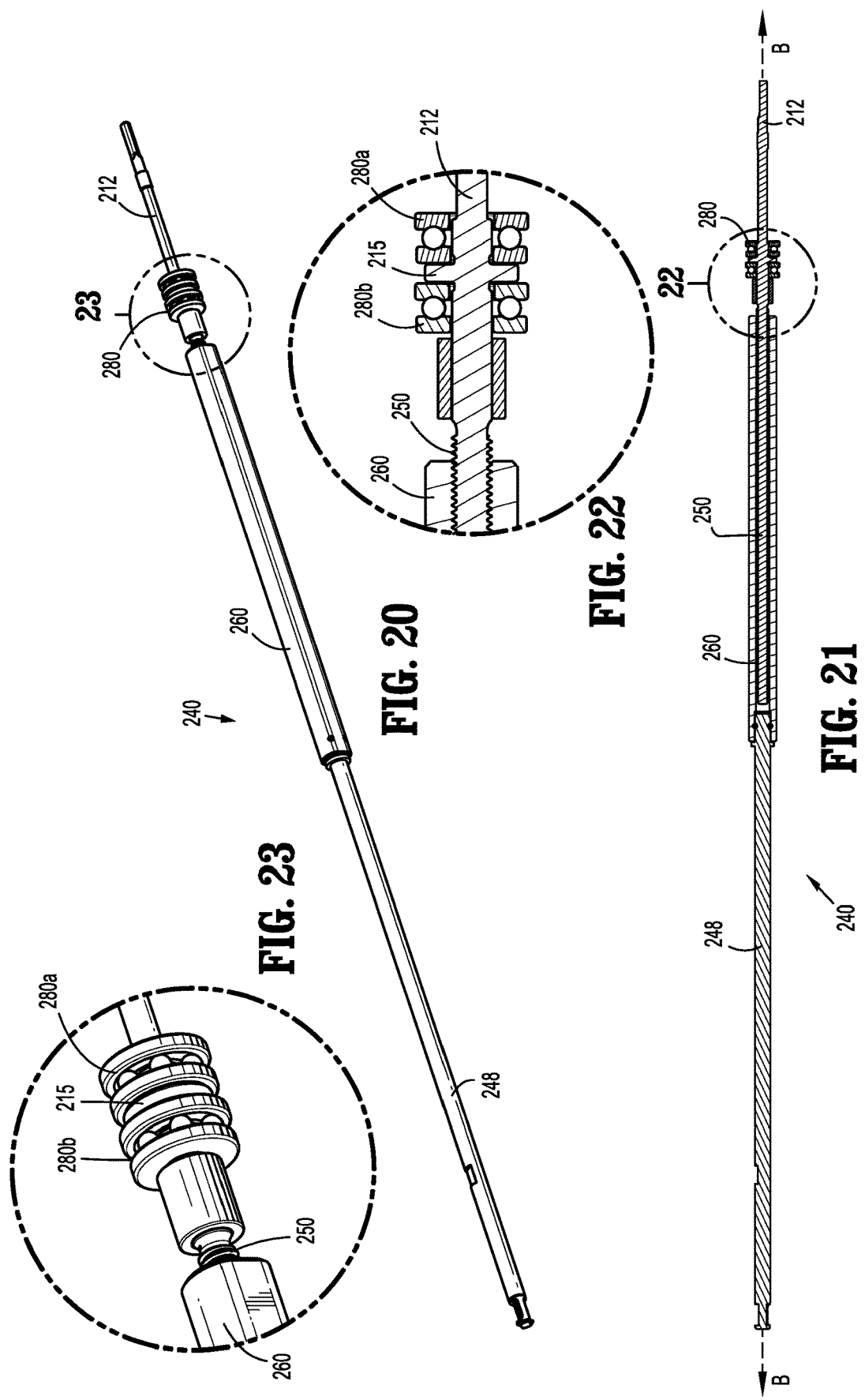

HAND HELD SURGICAL HANDLE ASSEMBLY, SURGICAL ADAPTERS FOR USE BETWEEN SURGICAL HANDLE ASSEMBLY AND SURGICAL LOADING UNITS, AND METHODS OF USE

CROSS-REFERENCE TO RELATED APPLICATIONS

The present application is a continuation of U.S. patent application Ser. No. 15/867,914, filed on Jan. 11, 2018, which is a continuation of U.S. patent application Ser. No. 13/887,402, filed on May 6, 2013, now U.S. Pat. No. 9,868,198, which claims the benefit of and priority to a U.S. Provisional Application No. 61/654,206, filed on Jun. 1, 2012, the entire disclosures of all of the foregoing applications are incorporated by reference herein.

BACKGROUND

1. Technical Field

The present disclosure relates to surgical devices and/or systems, surgical adapters and their methods of use. More specifically, the present disclosure relates to hand held powered surgical devices, surgical adapters and/or adapter assemblies for use between and for interconnecting the powered, rotating and/or articulating surgical device or handle assembly and an loading unit for clamping, cutting and/or stapling tissue.

2. Background of Related Art

One type of surgical device is a linear clamping, cutting and stapling device. Such a device may be employed in a surgical procedure to resect a cancerous or anomalous tissue from a gastro-intestinal tract. Conventional linear clamping, cutting and stapling instruments include a pistol grip-styled structure having an elongated shaft and distal portion. The distal portion includes a pair of scissors-styled gripping elements, which clamp the open ends of the colon closed. In this device, one of the two scissors-styled gripping elements, such as the anvil portion, moves or pivots relative to the overall structure, whereas the other gripping element remains fixed relative to the overall structure. The actuation of this scissoring device (the pivoting of the anvil portion) is controlled by a grip trigger maintained in the handle.

In addition to the scissoring device, the distal portion also includes a stapling mechanism. The fixed gripping element of the scissoring mechanism includes a staple cartridge receiving region and a mechanism for driving the staples up through the clamped end of the tissue against the anvil portion, thereby sealing the previously opened end. The scissoring elements may be integrally formed with the shaft or may be detachable such that various scissoring and stapling elements may be interchangeable.

A number of surgical device manufacturers have developed product lines with proprietary drive systems for operating and/or manipulating the surgical device. In many instances the surgical devices include a handle assembly, which is reusable, and a disposable loading unit or the like that is selectively connected to the handle assembly prior to use and then disconnected from the loading unit following use in order to be disposed of or in some instances sterilized for re-use.

Many of the existing loading units for use with many of the existing surgical devices and/or handle assemblies are driven by a linear force. For examples, loading units for performing endo-gastrointestinal anastomosis procedures, end-to-end anastomosis procedures and transverse anastomosis procedures, each typically require a linear driving force in order to be operated. As such, these loading units are not compatible with surgical devices and/or handle assemblies that use a rotary motion to deliver power or the like.

In order to make the linear driven loading units compatible with surgical devices and/or handle assemblies that use a rotary motion to deliver power, a need exists for adapters and/or adapter assemblies to interface between and interconnect the linear driven loading units with the rotary driven surgical devices and/or handle assemblies.

SUMMARY

The present disclosure relates to a surgical device, comprising a device housing, at least one drive motor, a battery, a circuit board, a loading unit, and an adapter assembly. The device housing defines a connecting portion for selectively connecting with the adapter assembly. The at least one drive motor is supported in the device housing and is configured to rotate at least one drive shaft. The battery is disposed in electrical communication with the at least one drive motor. The circuit board is disposed within the housing for controlling power delivered from the battery to the at least one drive motor. The loading unit is configured to perform at least one function, and includes at least one axially translatable drive member. The adapter assembly is for selectively interconnecting the loading unit and the device housing, and includes a knob housing, and at least one drive converter assembly. The knob housing is configured and adapted for selective connection to the device housing and to be in operative communication with each of the at least one rotatable drive shaft. The at least one drive converter assembly is for interconnecting a respective one of the at least one rotatable drive shaft and one of the at least one axially translatable drive member of the loading unit. The at least one drive converter assembly converts and transmits a rotation of the rotatable drive shaft to an axial translation of the at least one axially translatable drive member of the loading unit. The at least one drive converter assembly includes a first drive converter assembly including a drive element, a drive nut, and a distal drive member. The drive element is rotatably supported in the knob housing. A proximal end of the drive element is engagable with the rotatable drive shaft. The drive element defines a longitudinal axis. The drive nut is threadably engaged with a distal portion of the drive element. A proximal portion of the distal drive member is disposed in mechanical cooperation with the drive nut. A distal portion of the distal drive member is configured for selective engagement with the at least one axially translatable drive member of the loading unit. Rotation of the rotatable drive shaft results in rotation of the drive element. Rotation of the drive element results in axial translation of the drive nut, the distal drive member, and the at least one axially translatable drive member of the loading unit. The drive nut is disposed about the longitudinal axis, and the distal drive member is disposed along the longitudinal axis.

In disclosed embodiments, the threaded portion of the drive element is disposed along the longitudinal axis.

In disclosed embodiments, a radial center of each of the drive element, the drive nut and the distal drive member are disposed along the longitudinal axis.

In disclosed embodiments, a radial center of the threaded portion of the drive element is disposed along the longitudinal axis.

In disclosed embodiments, the entire lengths of each of the drive element, and the distal drive member are disposed along the longitudinal axis, and wherein the entire length of the drive nut is disposed about the longitudinal axis.

In disclosed embodiments, the drive element is radially off-center with respect to the knob housing. Here, it is disclosed that the drive shaft is radially off-center with respect to the connecting portion.

In disclosed embodiments, the drive is rotatable with respect to the drive nut. Here, it is disclosed that the distal drive member is fixed from rotation with respect to the drive nut.

The present disclosure also relates to an adapter assembly for selectively interconnecting a surgical loading unit and a handle assembly having at least one rotatable drive shaft. The adapter assembly comprises a knob housing, and at least one drive converter assembly. The knob housing is configured and adapted for selective connection to a handle assembly, and includes a drive coupling housing. The at least one drive converter assembly is for interconnecting a respective one of the at least one rotatable drive shaft and a portion of a surgical loading unit. The at least one drive converter assembly converts and transmits a rotation of the rotatable drive shaft to an axial translation of the at least one axially translatable drive member of the loading unit. The at least one drive converter assembly includes a first drive converter assembly including a drive element, a drive nut, and a distal drive member. The drive element is rotatably supported in the knob housing. A proximal end of the drive element is engagable with the rotatable drive shaft. The drive element defines a longitudinal axis. The drive nut is threadably engaged with a distal portion of the drive element. A proximal portion of the distal drive member is disposed in mechanical cooperation with the drive nut. A distal portion of the distal drive member is configured for selective engagement with the at least one axially translatable drive member of the loading unit. Rotation of the rotatable drive shaft results in rotation of the drive element, and rotation of the drive element results in axial translation of the drive nut, the distal drive member, and the at least one axially translatable drive member of the loading unit. The drive nut is disposed about the longitudinal axis, and the distal drive member is disposed along the longitudinal axis.

In disclosed embodiments, the threaded portion of the drive element is disposed along the longitudinal axis.

In disclosed embodiments, a radial center of each of the drive element, the drive nut and the distal drive member are disposed along the longitudinal axis. Here, it is disclosed that a radial center of the threaded portion of the drive element is disposed along the longitudinal axis.

In disclosed embodiments, the entire lengths of each of the drive element, and the distal drive member are disposed along the longitudinal axis, and wherein the entire length of the drive nut is disposed about the longitudinal axis.

In disclosed embodiments, the drive element is radially off-center with respect to the knob housing.

In disclosed embodiments, the drive is rotatable with respect to the drive nut. Here, it is disclosed that the distal drive member is fixed from rotation with respect to the drive nut.

BRIEF DESCRIPTION OF THE DRAWINGS

Embodiments of the present disclosure are described herein with reference to the accompanying drawings, wherein:

FIG. 3 is a perspective view, with parts separated, of the surgical device of FIGS. 1 and 2;

FIG. 4 is a perspective view of a battery for use in the surgical device of FIGS. 1-3;

FIG. 5 is a perspective view of the surgical device of FIGS. 1-3, with a housing thereof removed;

FIG. 20 is a perspective view of a firing system of the present disclosure;

FIG. 21 is a longitudinal cross-sectional view of the firing system of FIG. 20;

FIG. 22 is an enlarged view of the indicated area of detail of FIG. 21;

FIG. 23 is an enlarged view of the indicated area of detail of FIG. 20;

DETAILED DESCRIPTION OF EMBODIMENTS

Figure 1:
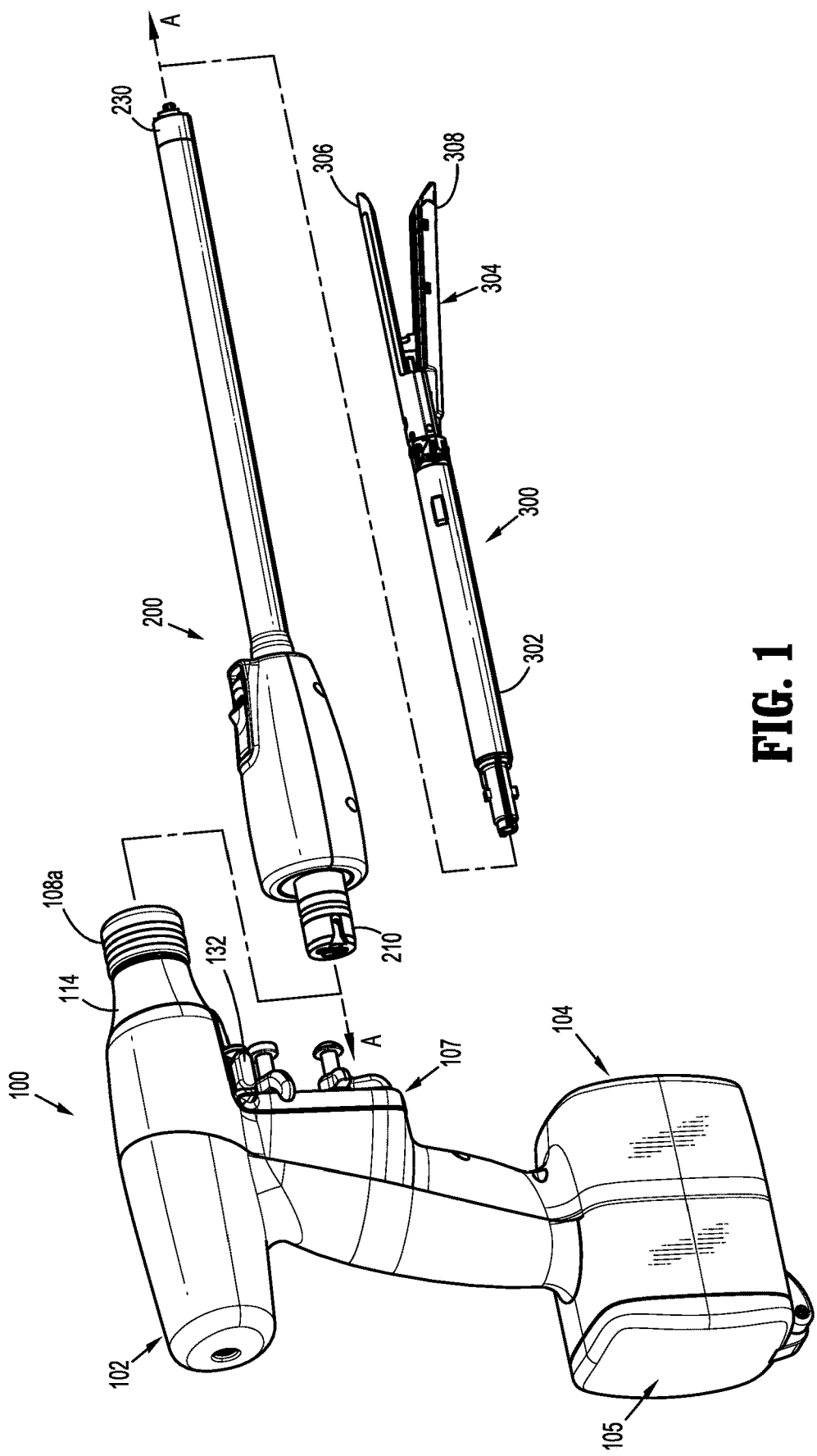
FIG. 1 is a perspective view, with parts separated, of a surgical device and adapter, in accordance with an embodiment of the present disclosure, illustrating a connection thereof with an loading unit.

Embodiments of the presently disclosed surgical devices, and adapter assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical instrument configured for selective attachment thereto of a plurality of different loading units that are each configured for actuation and manipulation by the powered hand held electromechanical surgical instrument.

As illustrated in FIG. 1, surgical device 100 is configured for selective connection with an adapter 200, and, in turn, adapter 200 is configured for selective connection with an loading unit or single use loading unit 300.

Figure 2:
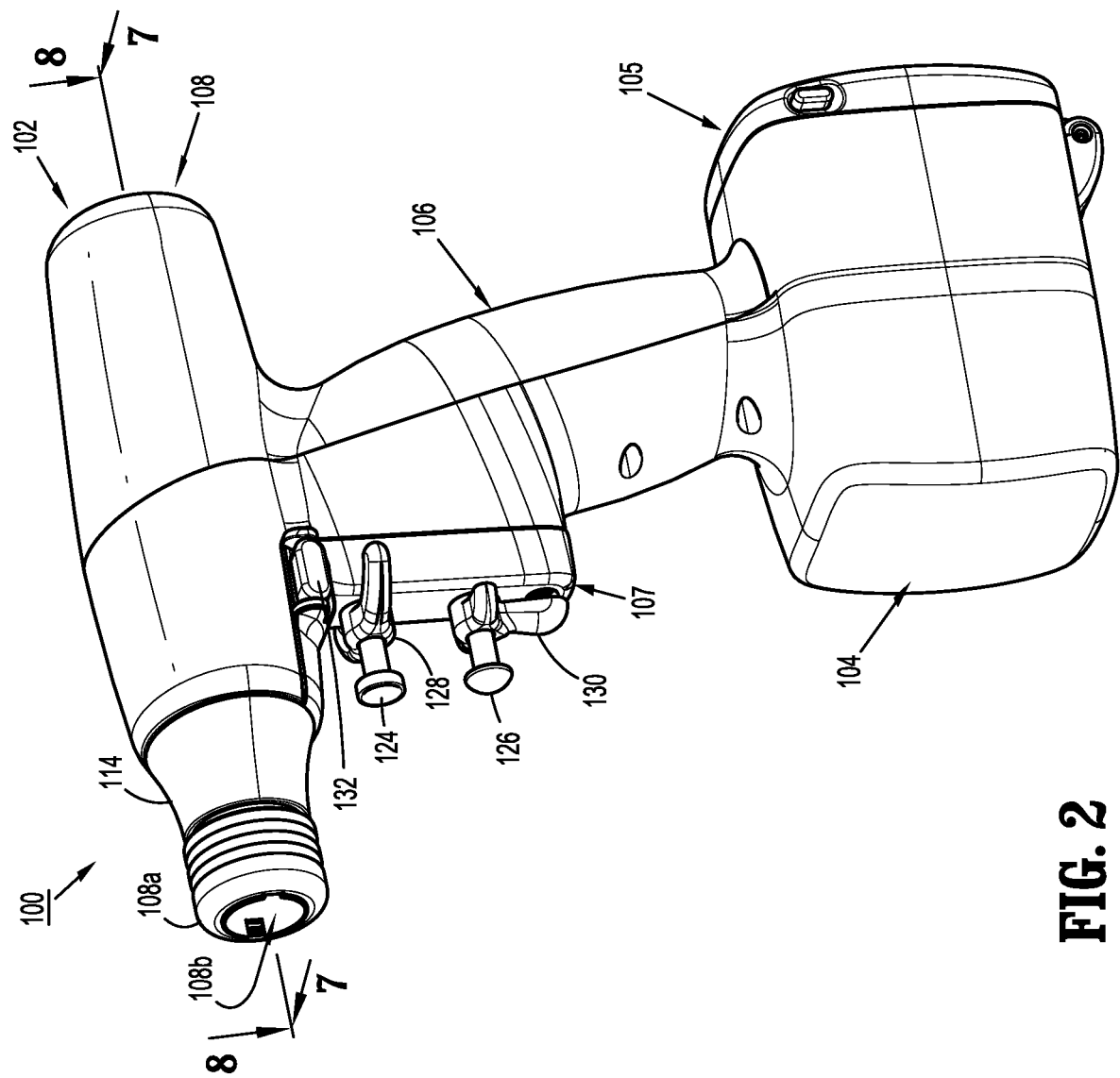
FIG. 2 is a perspective view of the surgical device of FIG. 1.

As illustrated in FIGS. 1-3, surgical device 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 is situated.

Distal and proximal half-sections 110a, 110b are divided along a plane that traverses a longitudinal axis "X" of upper housing portion 108, as seen in FIG. 3.

Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical device 100, as will be set forth in additional detail below.

Lower housing portion 104 of surgical device 100 defines an aperture (not shown) formed in an upper surface thereof and which is located beneath or within intermediate housing portion 106. The aperture of lower housing portion 104 provides a passage through which wires 152 pass to electrically interconnect electrical components (a battery 156, as illustrated in FIG. 4, a circuit board 154, as illustrated in FIG. 3, etc.) situated in lower housing portion 104 with electrical components (circuit board 150, drive mechanism 160, etc.) situated in intermediate housing portion 106 and/or upper housing portion 108.

Handle housing 102 includes a gasket 103 disposed within the aperture of lower housing portion 104 (not shown) thereby plugging or sealing the aperture of lower housing portion 104 while allowing wires 152 to pass therethrough. Gasket 103 functions to establish an air-tight seal between lower housing portion 106 and intermediate housing portion 108 such that circuit board 150 and drive mechanism 160 are protected from sterilization and/or cleaning procedures.

As shown, lower housing portion 104 of handle housing 102 provides a housing in which a rechargeable battery 156, is removably situated. Battery 156 is configured to supply power to any of the electrical components of surgical device 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

With reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent material. An illumination member 116 is disposed within nose cone 114 such that illumination member 116 is visible therethrough. Illumination member 116 is in the form of a light emitting diode printed circuit board (LED PCB). Illumination member 116 is configured to illuminate multiple colors with a specific color pattern being associated with a unique discrete event.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical device 100. In particular, drive mechanism 160 is configured to drive shafts and/or gear components in order to selectively move tool assembly 304 of loading unit 300 (see FIGS. 1 and 20) relative to proximal body portion 302 of loading unit 300, to rotate loading unit 300 about a longitudinal axis "X" (see FIG. 3) relative to handle housing 102, to move anvil assembly 306 relative to cartridge assembly 308 of loading unit 300, and/or to fire a stapling and cutting cartridge within cartridge assembly 308 of loading unit 300.

The drive mechanism 160 includes a selector gearbox assembly 162 that is located immediately proximal relative to adapter 200. Proximal to the selector gearbox assembly 162 is a function selection module 163 having a first motor 164 that functions to selectively move gear elements within the selector gearbox assembly 162 into engagement with an input drive component 165 having a second motor 166.

As illustrated in FIGS. 1-4, and as mentioned above, distal half-section 110a of upper housing portion 108 defines a connecting portion 108a configured to accept a corresponding drive coupling assembly 210 of adapter 200.

Figure 6:
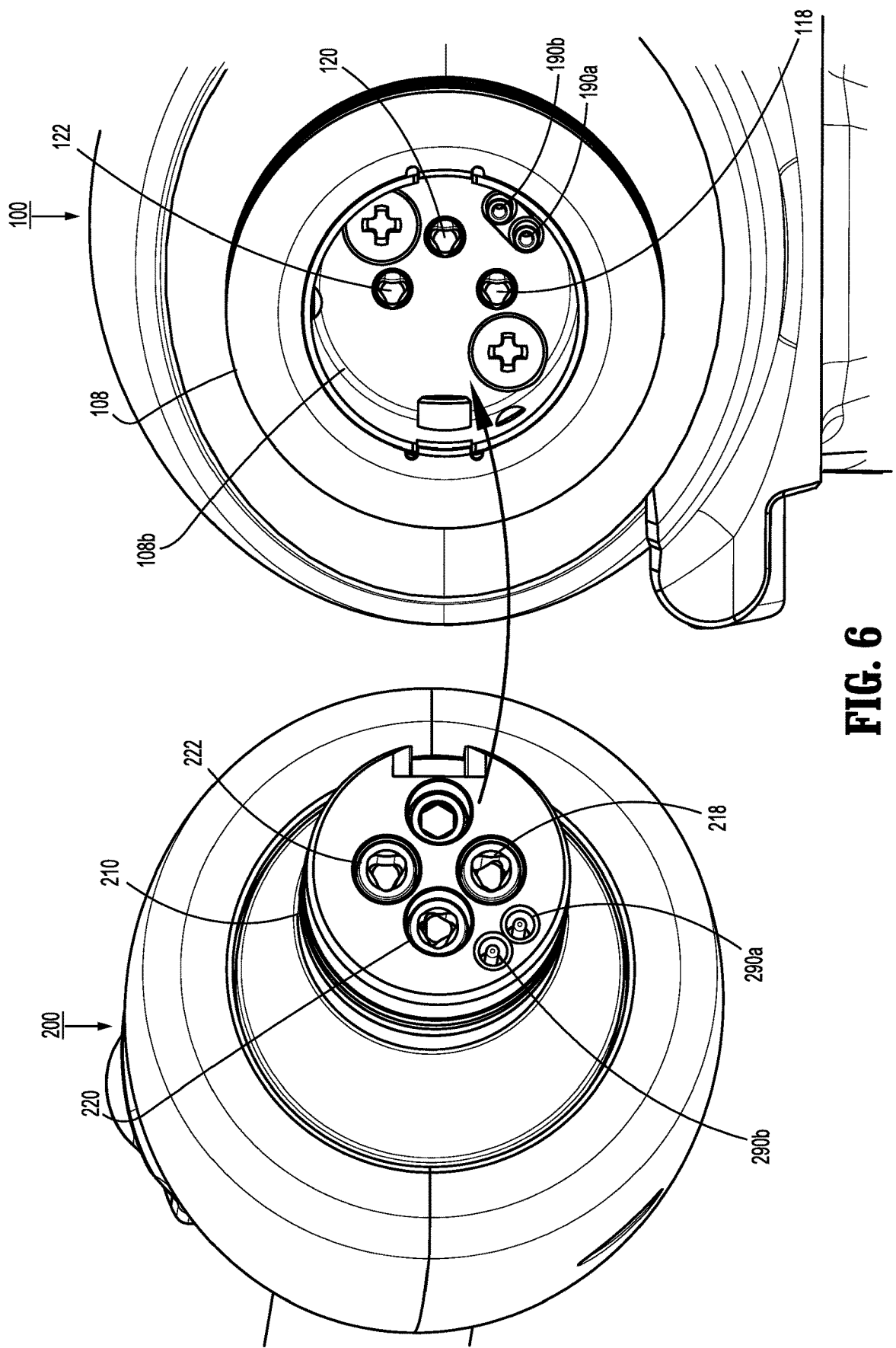
FIG. 6 is a perspective view of the connecting ends of each of the surgical device and the adapter, illustrating a connection therebetween.
Figure 7:
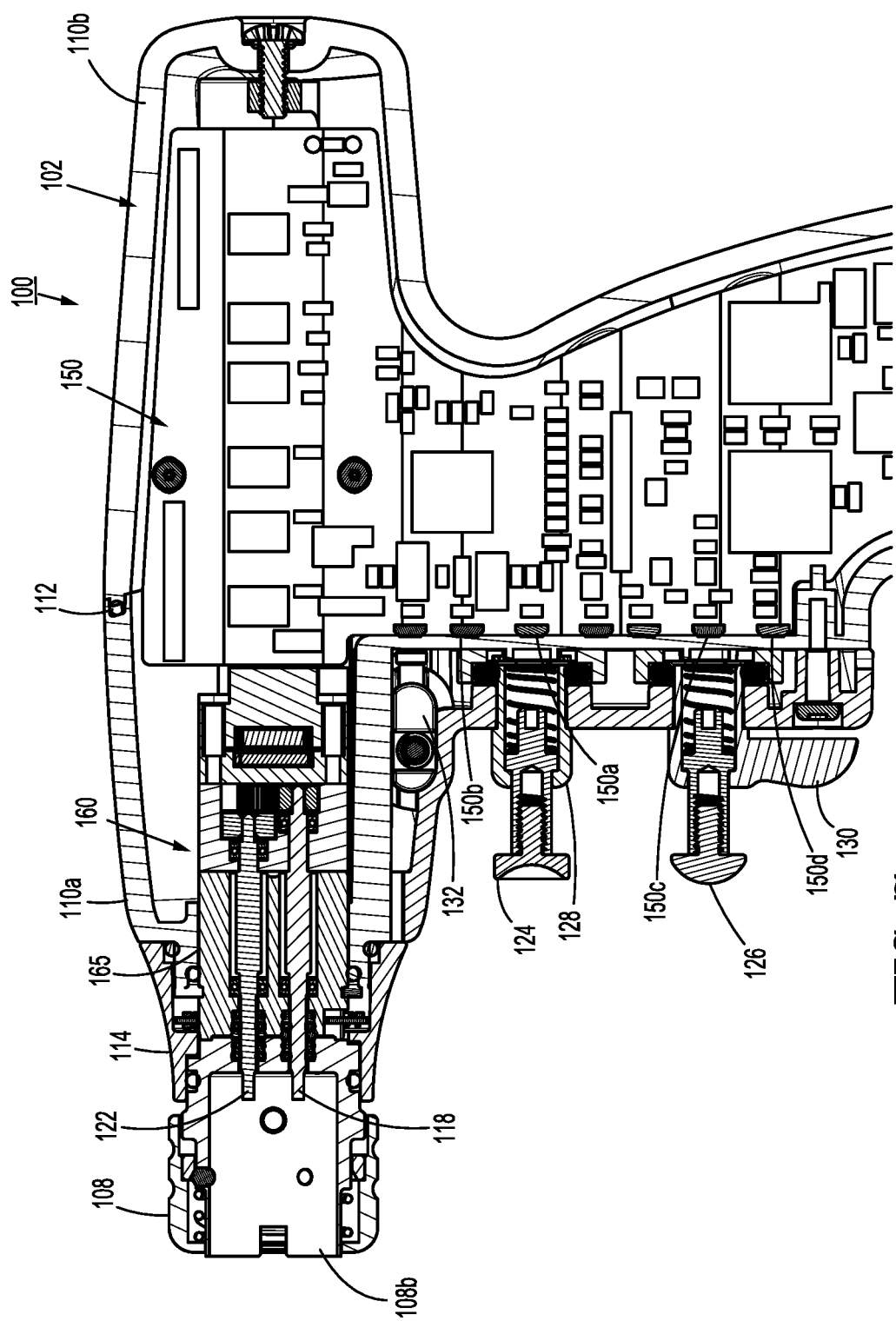
FIG. 7 is a cross-sectional view of the surgical device of FIGS. 1-3, as taken through 7-7 of FIG. 2.
Figure 8:
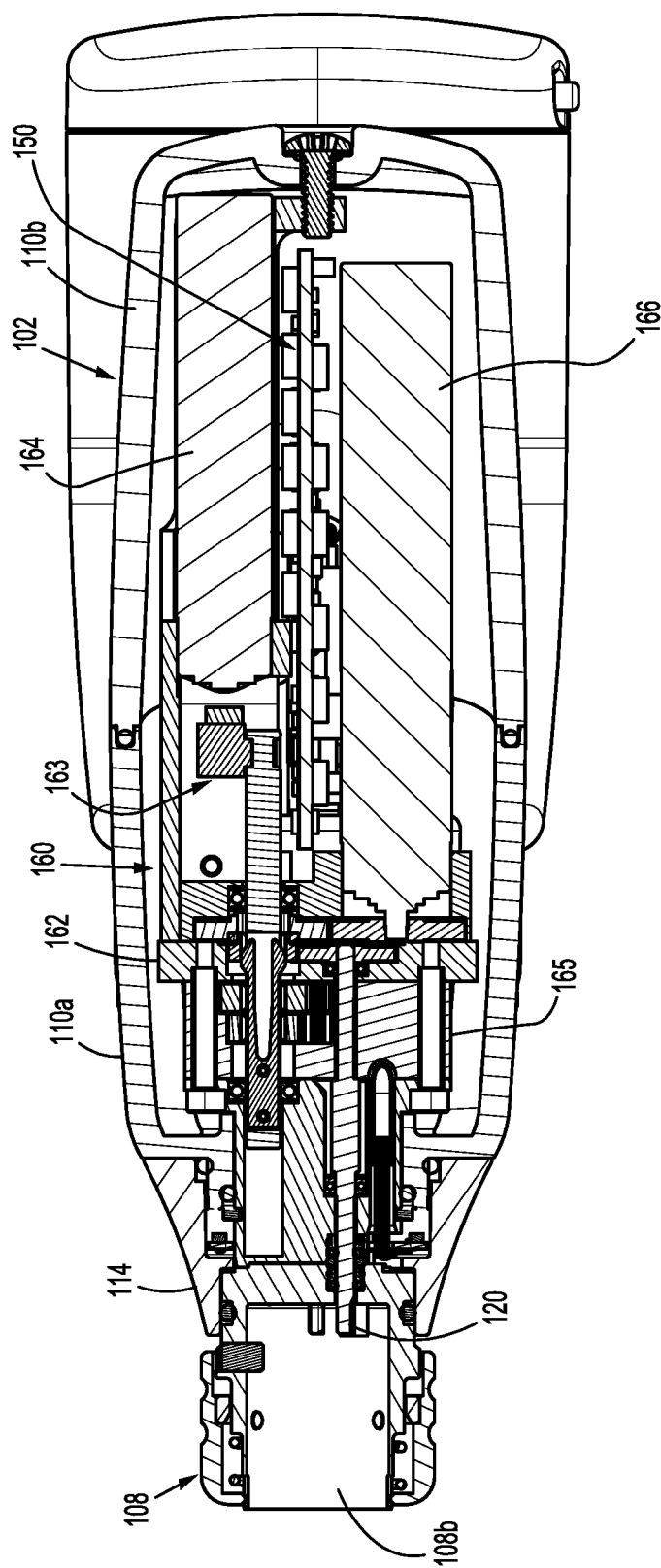
FIG. 8 is a cross-sectional view of the surgical device of FIGS. 1-3, as taken through 8-8 of FIG. 2.
Figure 9:
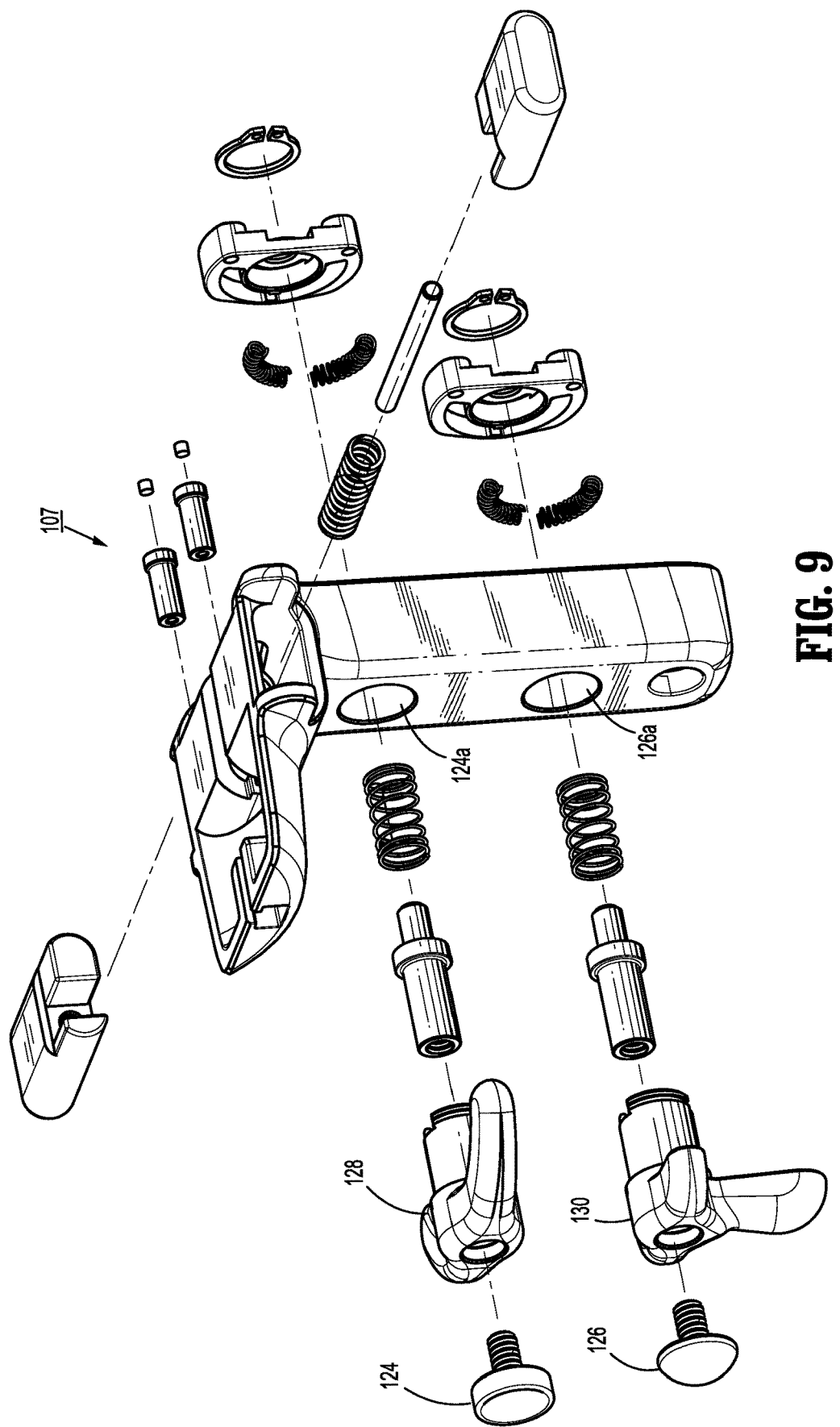
FIG. 9 is a perspective view, with parts separated, of a trigger housing of the surgical device of FIGS. 1-3.

As illustrated in FIGS. 6-8, connecting portion 108a of surgical device 100 has a cylindrical recess 108b that receives a drive coupling assembly 210 of adapter 200 when adapter 200 is mated to surgical device 100. Connecting portion 108a houses three rotatable drive connectors 118, 120, 122.

When adapter 200 is mated to surgical device 100, each of rotatable drive connectors 118, 120, 122 of surgical device 100 couples with a corresponding rotatable connector sleeve 218, 220, 222 of adapter 200. (see FIG. 6). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter 200.

The mating of drive connectors 118, 120, 122 of surgical device 100 with connector sleeves 218, 220, 222 of adapter 200 allows rotational forces to be independently transmitted via each of the three respective connector interfaces. The drive connectors 118, 120, 122 of surgical device 100 are configured to be independently rotated by drive mechanism 160. In this regard, the function selection module 163 of drive mechanism 160 selects which drive connector or connectors 118, 120, 122 of surgical device 100 is to be driven by the input drive component 165 of drive mechanism 160.

Since each of drive connectors 118, 120, 122 of surgical device 100 has a keyed and/or substantially non-rotatable interface with respective connector sleeves 218, 220, 222 of adapter 200, when adapter 200 is coupled to surgical device 100, rotational force(s) are selectively transferred from drive mechanism 160 of surgical device 100 to adapter 200.

The selective rotation of drive connector(s) 118, 120 and/or 122 of surgical device 100 allows surgical device 100 to selectively actuate different functions of loading unit 300. As will be discussed in greater detail below, selective and independent rotation of first drive connector 118 of surgical device 100 corresponds to the selective and independent opening and closing of tool assembly 304 of loading unit 300, and driving of a stapling/cutting component of tool assembly 304 of loading unit 300. Also, the selective and independent rotation of second drive connector 120 of surgical device 100 corresponds to the selective and independent articulation of tool assembly 304 of loading unit 300 transverse to longitudinal axis "X" (see FIG. 3). Additionally, the selective and independent rotation of third drive connector 122 of surgical device 100 corresponds to the selective and independent rotation of loading unit 300 about longitudinal axis "X" (see FIG. 3) relative to handle housing 102 of surgical device 100.

As mentioned above and as illustrated in FIGS. 5 and 8, drive mechanism 160 includes a selector gearbox assembly 162; a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical device 100 at a given time.

As illustrated in FIGS. 1-3 and FIG. 9, handle housing 102 supports a trigger housing 107 on a distal surface or side of intermediate housing portion 108. Trigger housing 107, in cooperation with intermediate housing portion 108, supports a pair of finger-actuated control buttons 124, 126 and rocker devices 128, 130. In particular, trigger housing 107 defines an upper aperture 124a for slidably receiving a first control button 124, and a lower aperture 126b for slidably receiving a second control button 126.

Each one of the control buttons 124, 126 and rocker devices 128, 130 includes a respective magnet (not shown) that is moved by the actuation of an operator. In addition, circuit board 150 includes, for each one of the control buttons 124, 126 and rocker devices 128, 130, respective Hall-effect switches 150a-150d that are actuated by the movement of the magnets in the control buttons 124, 126 and rocker devices 128, 130. In particular, located immediately proximal to the control button 124 is a first Hall-effect switch 150a (see FIGS. 3 and 7) that is actuated upon the movement of a magnet within the control button 124 upon the operator actuating control button 124. The actuation of first Hall-effect switch 150a, corresponding to control button 124, causes circuit board 150 to provide appropriate signals to function selection module 163 and input drive component 165 of the drive mechanism 160 to close a tool assembly 304 of loading unit 300 and/or to fire a stapling/cutting cartridge within tool assembly 304 of loading unit 300.

Also, located immediately proximal to rocker device 128 is a second Hall-effect switch 150b (see FIGS. 3 and 7) that is actuated upon the movement of a magnet (not shown) within rocker device 128 upon the operator actuating rocker device 128. The actuation of second Hall-effect switch 150b, corresponding to rocker device 128, causes circuit board 150 to provide appropriate signals to function selection module 163 and input drive component 165 of drive mechanism 160 to articulate tool assembly 304 relative to body portion 302 of loading unit 300. Advantageously, movement of rocker device 128 in a first direction causes tool assembly 304 to articulate relative to body portion 302 in a first direction, while movement of rocker device 128 in an opposite, e.g., second, direction causes tool assembly 304 to articulate relative to body portion 302 in an opposite, e.g., second, direction.

Furthermore, located immediately proximal to control button 126 is a third Hall-effect switch 150c (see FIGS. 3 and 7) that is actuated upon the movement of a magnet (not shown) within control button 126 upon the operator actuating control button 126. The actuation of third Hall-effect switch 150c, corresponding to control button 126, causes circuit board 150 to provide appropriate signals to function selection module 163 and input drive component 165 of drive mechanism 160 to open tool assembly 304 of loading unit 300.

In addition, located immediately proximal to rocker device 130 is a fourth Hall-effect switch 150d (see FIGS. 3 and 7) that is actuated upon the movement of a magnet (not shown) within rocker device 130 upon the operator actuating rocker device 130. The actuation of fourth Hall-effect switch 150d, corresponding to rocker device 130, causes circuit board 150 to provide appropriate signals to function selection module 163 and input drive component 165 of drive mechanism 160 to rotate loading unit 300 relative to handle housing 102 surgical device 100. Specifically, movement of rocker device 130 in a first direction causes loading unit 300 to rotate relative to handle housing 102 in a first direction, while movement of rocker device 130 in an opposite, e.g., second, direction causes loading unit 300 to rotate relative to handle housing 102 in an opposite, e.g., second, direction.

As seen in FIGS. 1-3, surgical device 100 includes a fire button or safety switch 132 supported between intermediate housing portion 108 and upper housing portion, and situated above trigger housing 107. In use, tool assembly 304 of loading unit 300 is actuated between opened and closed conditions as needed and/or desired. In order to fire loading unit 300, to expel fasteners therefrom when tool assembly 304 of loading unit 300 is in a closed condition, safety switch 132 is depressed thereby instructing surgical device 100 that loading unit 300 is ready to expel fasteners therefrom.

As illustrated in FIGS. 1 and 10-24, surgical device 100 is configured for selective connection with adapter 200, and, in turn, adapter 200 is configured for selective connection with loading unit 300.

Figure 25:
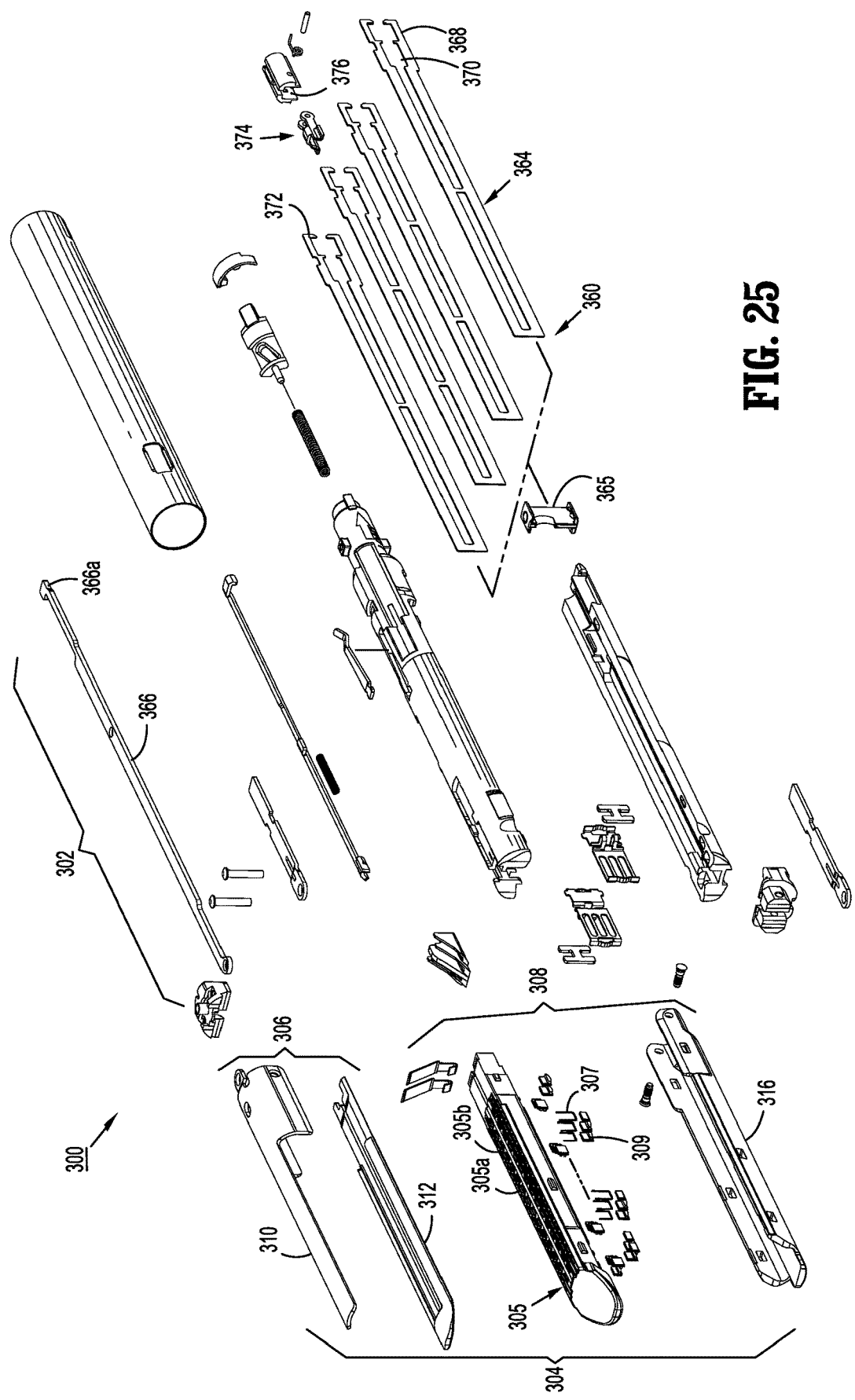
FIG. 25 is a perspective view, with parts separated, of an exemplary loading unit for use with the surgical device and the adapter of the present disclosure.

Adapter 200 is configured to convert a rotation of either of drive connectors 120 and 122 of surgical device 100 into axial translation useful for operating a drive assembly 360 and an articulation link 366 of loading unit 300, as illustrated in FIG. 25 and as will be discussed in greater detail below.

Adapter 200 includes a first drive transmitting/converting assembly for interconnecting third rotatable drive connector 122 of surgical device 100 and a first axially translatable drive member 360 of loading unit 300, wherein the first drive transmitting/converting assembly converts and transmits a rotation of third rotatable drive connector 122 of surgical device 100 to an axial translation of the first axially translatable drive assembly 360 of loading unit 300 for firing.

Adapter 200 includes a second drive transmitting/converting assembly for interconnecting second rotatable drive connector 120 of surgical device 100 and a second axially translatable drive member 366 of loading unit 300, wherein the second drive transmitting/converting assembly converts and transmits a rotation of second rotatable drive connector 120 of surgical device 100 to an axial translation of articulation link 366 of loading unit 300 for articulation.

Figures 10, 11:
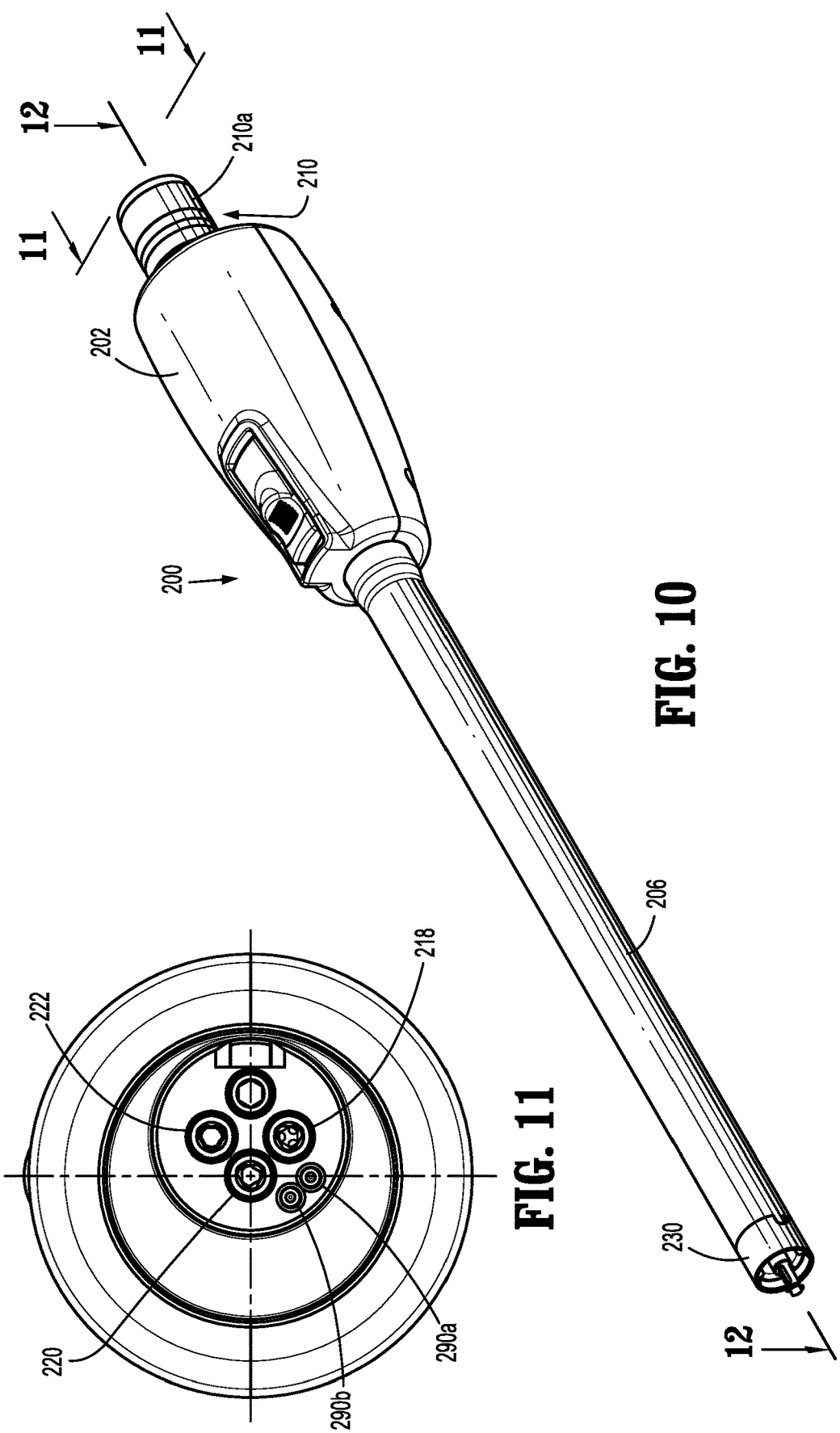
FIG. 10 is a perspective view of the adapter of FIG. 1.
FIG. 11 is an end view of the adapter of FIGS. 1 and 10, as seen from 11-11 of FIG. 10.

Turning now to FIG. 10, adapter 200 includes a knob housing 202 and an outer tube 206 extending from a distal end of knob housing 202. Knob housing 202 and outer tube 206 are configured and dimensioned to house the components of adapter 200. Outer tube 206 is dimensioned for endoscopic insertion, in particular, that outer tube is passable through a typical trocar port, cannula or the like. Knob housing 202 is dimensioned to not enter the trocar port, cannula of the like. Knob housing 202 is configured and adapted to connect to connecting portion 108a of upper housing portion 108 of distal half-section 110a of surgical device 100.

Figure 12:
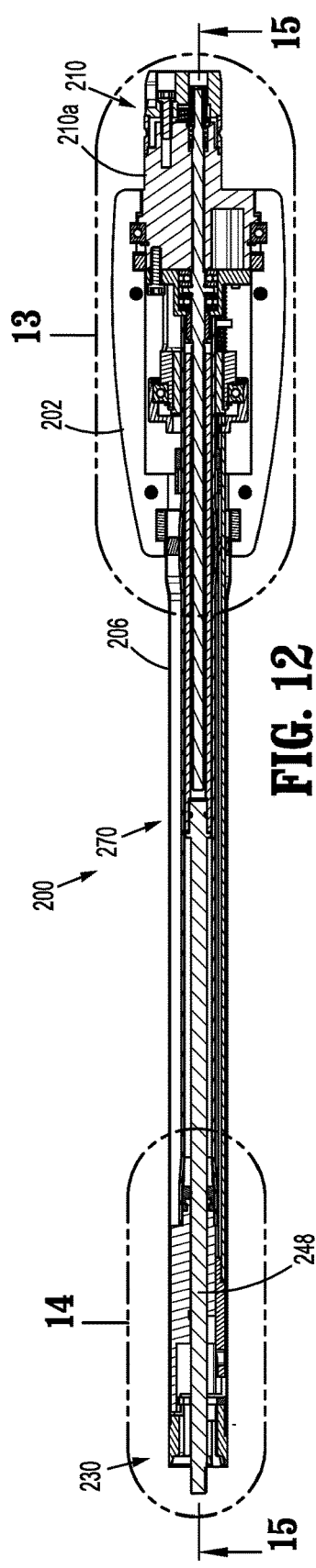
FIG. 12 is a cross-sectional view of the adapter of FIGS. 1 and 10, as taken through 12-12 of FIG. 10.
Figure 15:
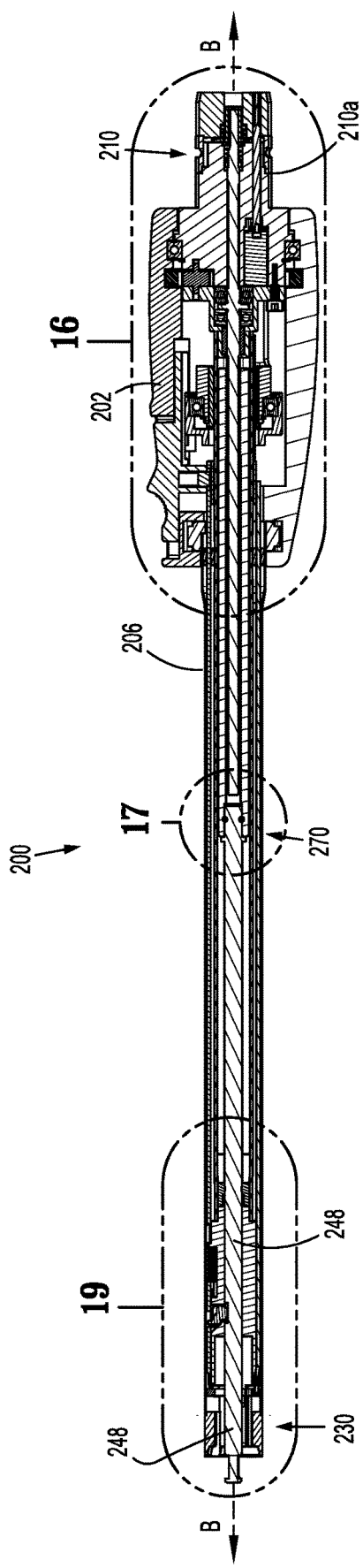
FIG. 15 is a cross-sectional view of the adapter of FIGS. 1 and 10, as taken through 15-15 of FIG. 12.

As seen in FIGS. 10, 12 and 15, adapter 200 includes a surgical device drive coupling assembly 210 at a proximal end thereof and an loading unit coupling assembly 230 at a distal end thereof. Drive coupling assembly 210 includes a drive coupling housing 210a rotatably supported, at least partially, in knob housing 202. In the illustrated embodiments, drive coupling assembly 210 rotatably supports a first rotatable proximal drive shaft or element 212.

As seen in FIGS. 6 and 11, drive coupling housing 210a is configured to rotatably support first, second and third connector sleeves 218, 220 and 222, respectively. Each of connector sleeves 218, 220, 222 is configured to mate with respective first, second and third drive connectors 118, 120, 122 of surgical device 100, as described above. Connector sleeve 220 is also configured to mate with a proximal end of first proximal drive shaft 212. It is further envisioned that connector sleeves 218 and 222 are configured to mate with a proximal end of a second proximal drive shaft and a third proximal drive shaft, respectively.

Figure 13:
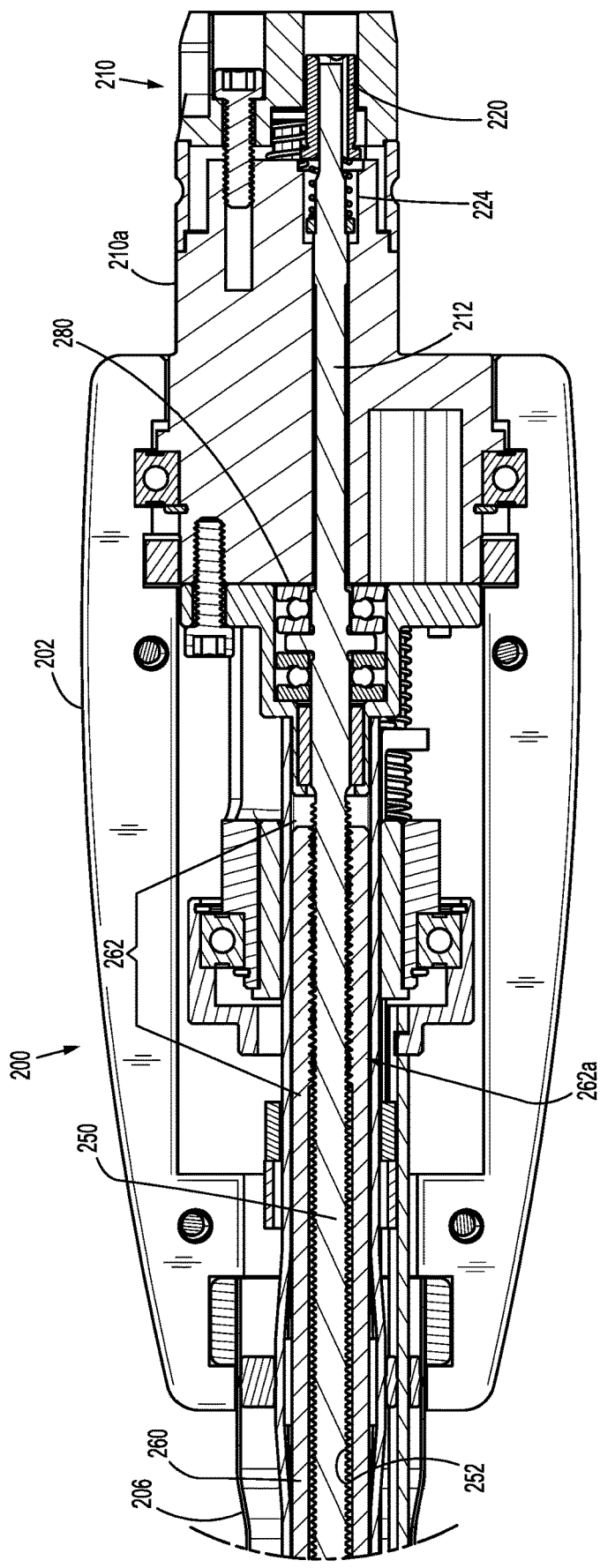
FIG. 13 is an enlarged view of the indicated area of detail of FIG. 12.
Figure 14:
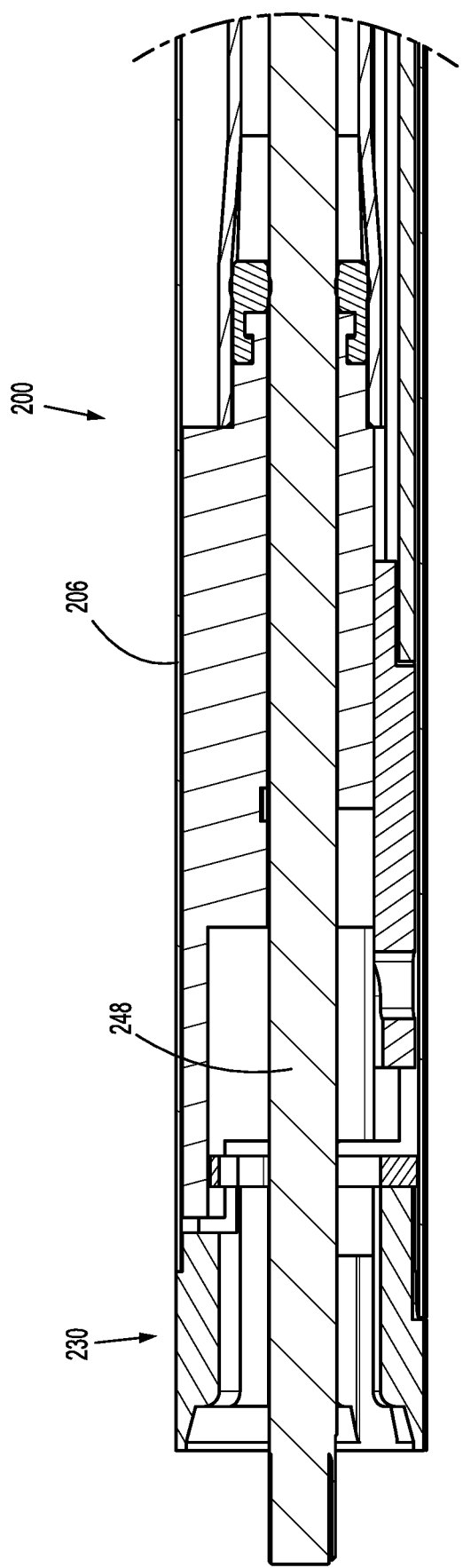
FIG. 14 is an enlarged view of the indicated area of detail of FIG. 12.
Figure 16:
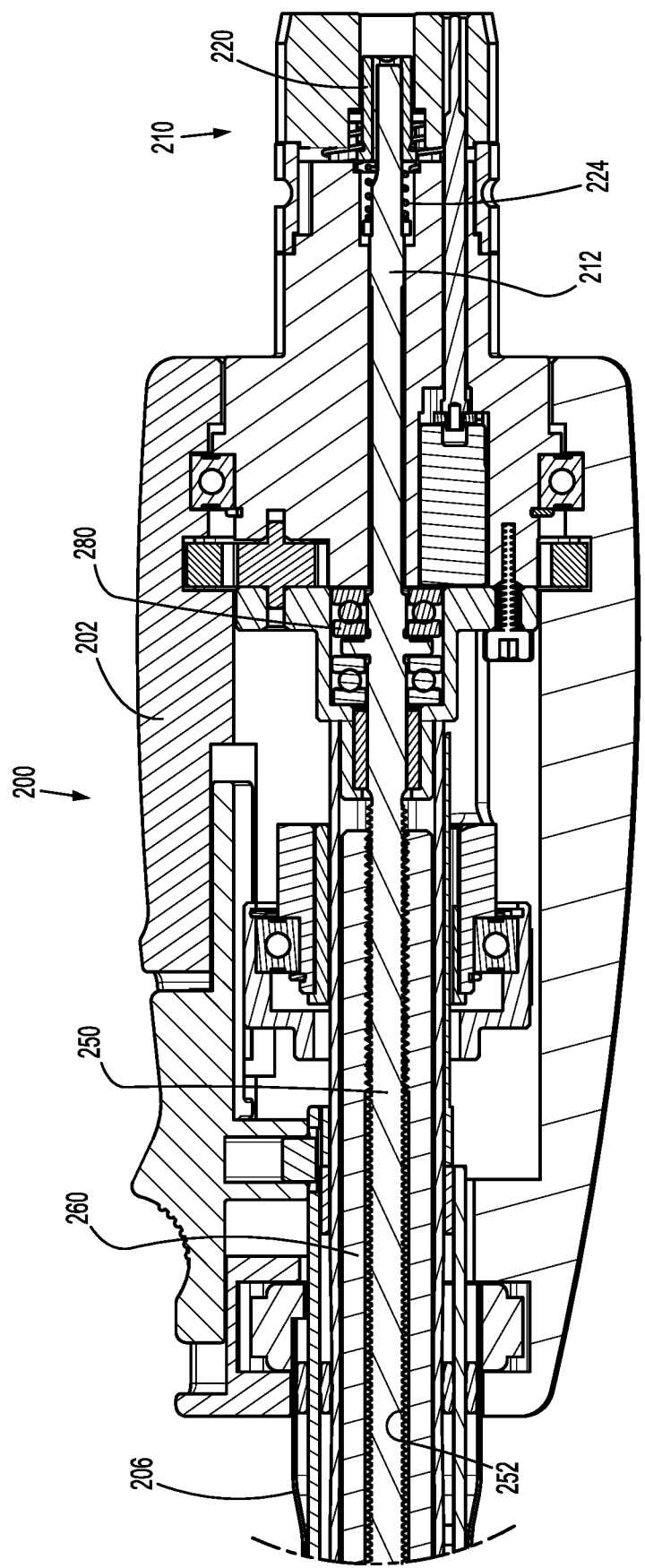
FIG. 16 is an enlarged view of the indicated area of detail of FIG. 15.

With particular reference to FIGS. 13 and 16, proximal drive coupling assembly 210 includes a biasing member 224 disposed distally of respective connector sleeve 220. Biasing member 224 is disposed about drive shaft 212. Biasing member 224 acts on connector sleeve 220 to help maintain connector sleeve 220 engaged with the distal end of rotatable drive connector 118 of surgical device 100 when adapter 200 is connected to surgical device 100.

In particular, biasing member 224 functions to bias connector sleeve 220 in a proximal direction. In this manner, during assembly of adapter 200 to surgical device 100, if connector sleeve 220 is misaligned with the drive connector 120 of surgical device 100, biasing member 224 is compressed. Thus, when drive mechanism 160 of surgical device 100 is engaged, drive connector 120 of surgical device 100 will rotate and biasing member 224 will cause connector sleeve 220 to slide back proximally, effectively coupling drive connector 120 of surgical device 100 to proximal drive shaft 212 of proximal drive coupling assembly 210. It is further envisioned that drive coupling assembly 210 includes respective biasing members for proximally biasing each connector sleeve 218, 222 into engagement with the distal end of respective rotatable drive connectors 118, 122.

Adapter 200, as seen in FIGS. 12, 15, 20 and 21, includes a drive transmitting/converting assembly 240 disposed within handle housing 202 and outer tube 206. Drive transmitting/converting assembly 240 is configured and adapted to transmit or convert a rotation of drive connector 120 of surgical device 100 into axial translation of a distal drive member 248 of adapter 200, to effectuate closing, opening, and firing of loading unit 300.

As seen in FIGS. 12-24, and particularly FIGS. 20-23, first drive transmitting/converting assembly 240 includes drive shaft 212, a lead screw 250, a drive nut 260, and distal drive member 248. Lead screw 250 is a threaded portion 252, distally disposed on drive shaft 212. Drive nut 260 is an elongated member and includes an internal threaded portion 262 along an internal periphery of at least a portion of its length (e.g., proximal portion 262a). Threaded portion 262 of drive nut 260 is configured to mechanically engage threaded portion 252 of lead screw 250. A proximal portion 248a of distal drive member 248 is disposed in mechanical cooperation with a distal portion 260b of drive nut 260 via a linking assembly 270.

Figure 17:
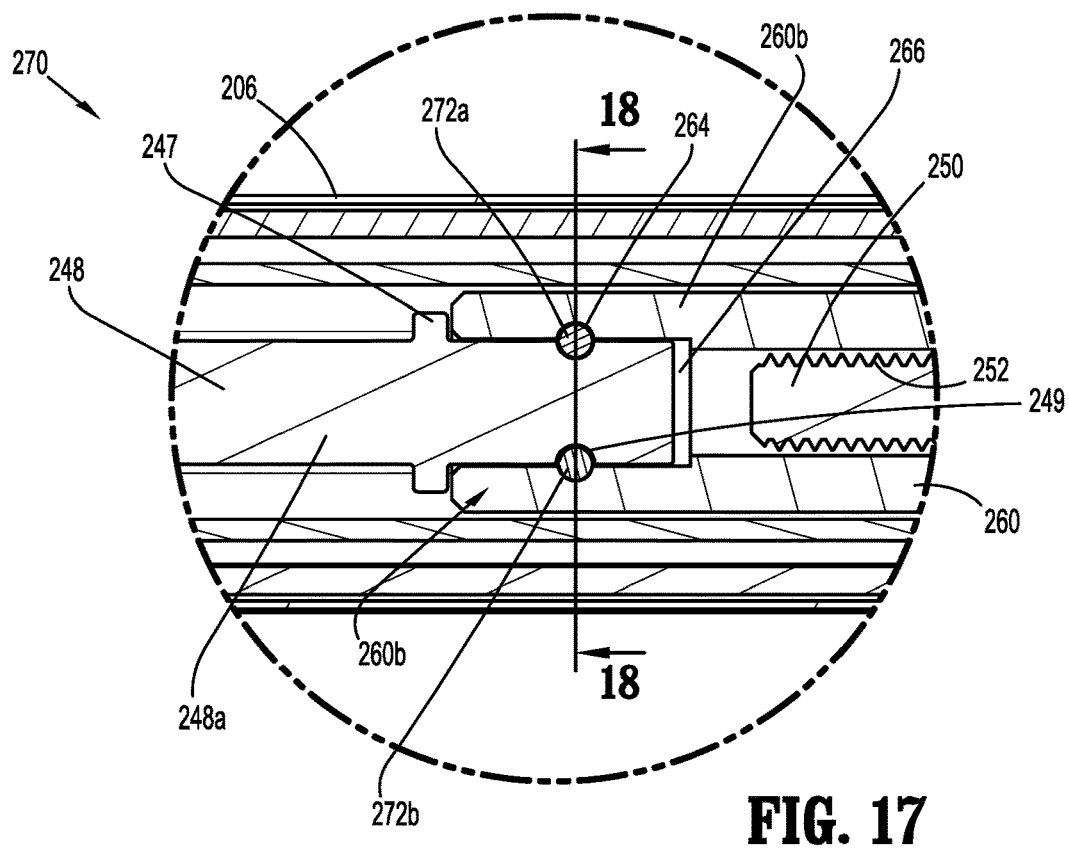
FIG. 17 is an enlarged view of the indicated area of detail of FIG. 15.
Figure 18:
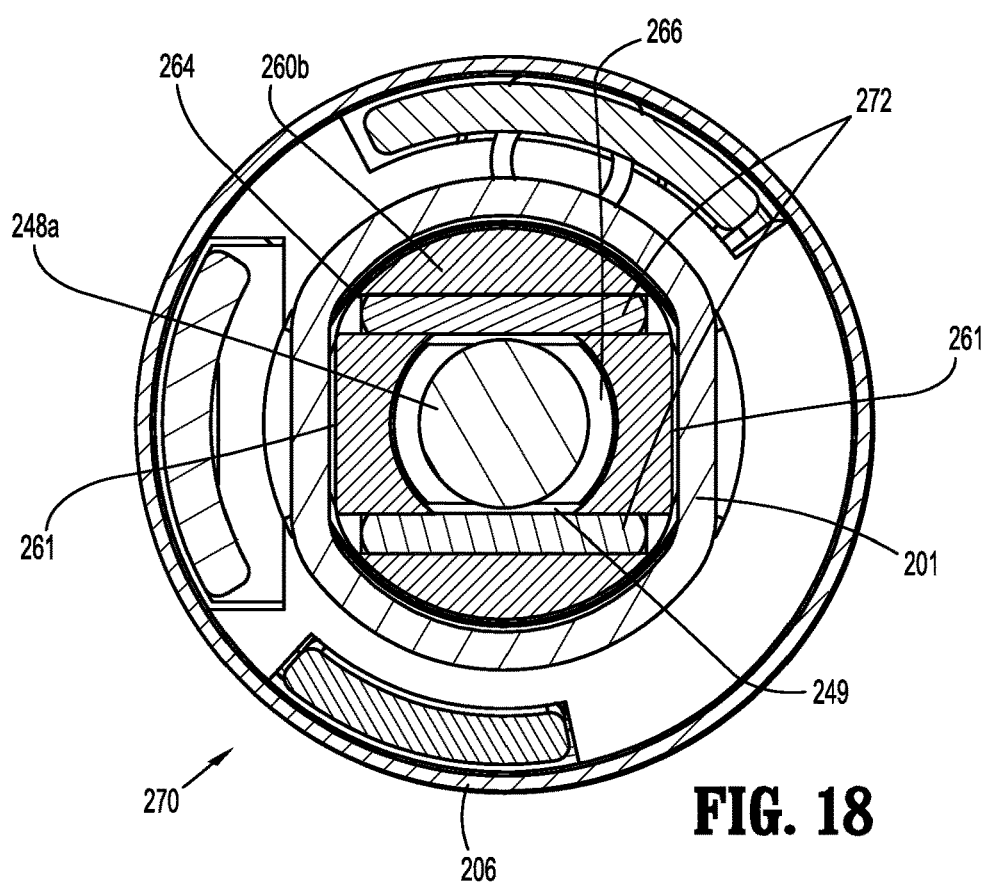
FIG. 18 is a cross-sectional view of the adapter of FIGS. 1 and 10, as taken through 18-18 of FIG. 17.
Figure 19:
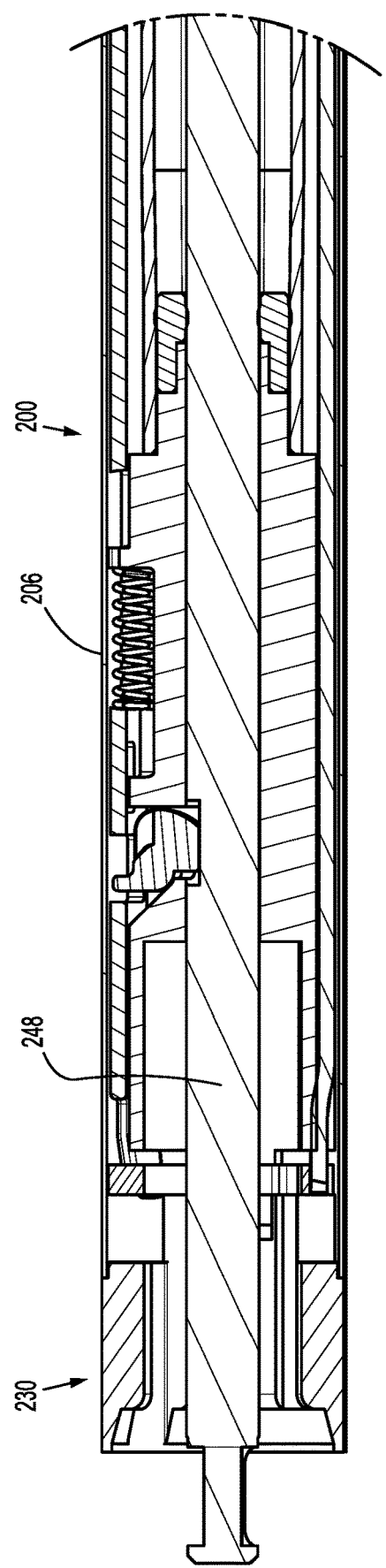
FIG. 19 is an enlarged view of the indicated area of detail of FIG. 15.
Figure 24:
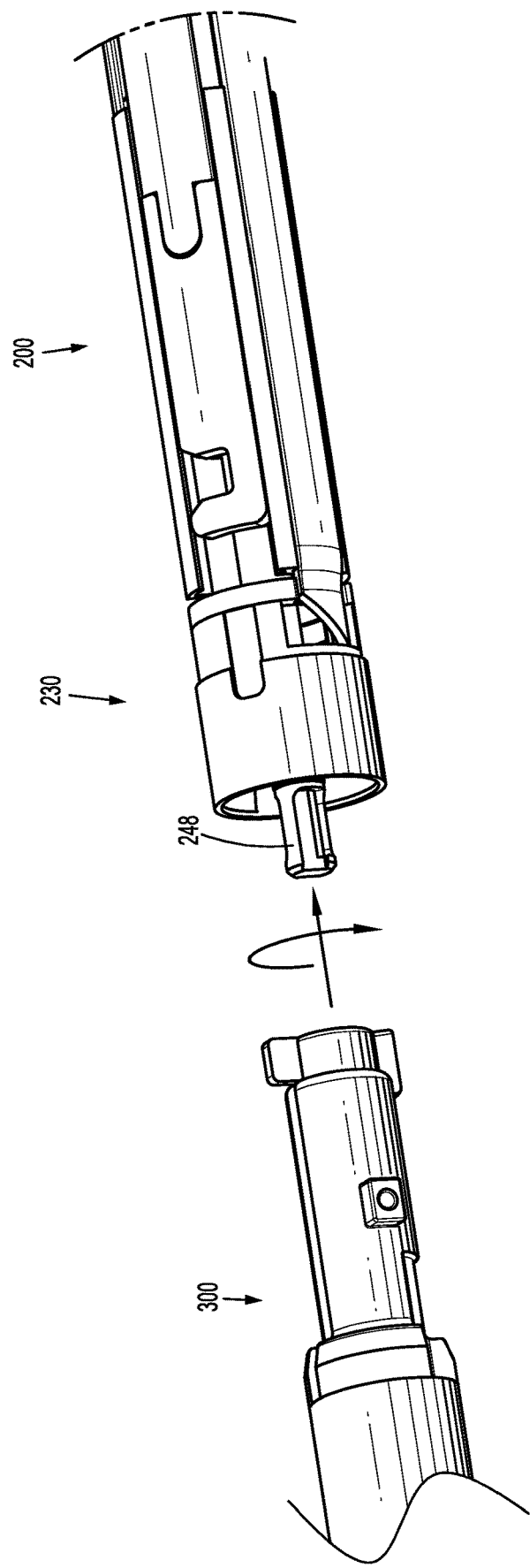
FIG. 24 is a perspective view of a distal portion of the adapter of FIGS. 1 and 10 adjacent a proximal portion of a loading unit.

In particular, with regard to FIGS. 15, 17 and 18, linking assembly 270 includes a first pin 272a and a second pin 272b disposed perpendicularly from a longitudinal axis B-B defined by drive shaft 212. Each pin 272 extends through a groove 264 (FIG. 17), which extends at least partially through drive nut 260, and a pair of corresponding recesses 249 (FIG. 18) extending at least partially through distal drive member 248. Additionally, a proximal portion 248a of distal drive member 248 is disposed within a socket 266 formed within a distal portion 260b of drive nut 260. Further, distal drive member 248 includes a stop member 247 disposed adjacent proximal portion 248a thereof, which is configured to help limit distal translation of drive nut 260 with respect to distal drive member 248, for instance. Accordingly, linking assembly 270, including pins 272, effectively couples drive nut 260 with distal drive member 248, such that longitudinal translation of drive nut 260 causes concomitant longitudinal translation of distal drive member 248.

Further, with particular reference to FIG. 18, at least a portion of the perimeter of drive nut 260 includes an anti-rotation section 261. Section 261 is shown including flat surfaces, which are disposed on two lateral sides of drive nut 260 and adjacent similarly-shaped surfaces 201 of an interior portion of adapter 200. Thus, while rotation of drive shaft 212 causes rotation of lead screw 250, and while rotation of lead screw 250 would ordinarily causes rotation and longitudinal translation of drive nut 260, anti-rotation section 261 of drive nut 260 eliminates the rotation component of its movement. Thus, rotation of drive shaft 212 causes a non-rotational, longitudinal translation of drive nut 260, and thus distal drive member 248.

With reference to FIGS. 20-23, first drive transmitting/converting assembly 240 also includes a pair of thrust bearings 280. In the illustrated embodiment, thrust bearings 280 are disposed circumferentially surrounding a portion of drive shaft 212, proximally of lead screw 250. Additionally, drive shaft 212 is shown including an enlarged-diameter ring or flange 215 disposed between a first thrust bearing 280a and a second thrust bearing 280b. It is envisioned that thrust bearings 280 facilitate rotation of drive shaft 212 with respect to drive coupling housing 210a, while maintaining the ability to rotate when drive shaft 212 is subjected to axial forces (e.g., when jaw members of end effector 300 are clamping tissue, etc.)

As shown in FIG. 21, longitudinal axis B-B extends through a radial center of drive shaft 212, a radial center of lead screw 250, a radial center of drive nut 260 (i.e., drive nut 260 is disposed about longitudinal axis B-B), and a radial center of distal drive member 248. Further, longitudinal axis B-B extends through the radial centers of drive shaft 212, lead screw 250, drive nut 260, and distal drive member 248 along the entirety of their respective lengths. This orientation of the so-called "on center drive system" allows distal drive member 248 to be driven directly from a motor (first motor 164, for example) and does not require any gears, thus reducing complexity and costs that are generally associated from a geared assembly. Additionally, since drive shaft 212 and lead screw 250 are under the same torque load, accurate monitoring of the torque from handle housing 102 can be facilitated.

In use, rotation of drive shaft 212, causes rotation of lead screw 250, which results in longitudinal translation of drive nut 260 along longitudinal axis B-B defined by drive shaft 212, which causes longitudinal translation of distal drive member 248. When end effector 300 is engaged with adapter 200, longitudinal translation of distal drive member 248 causes concomitant axial translation of drive member 374 of loading unit 300 to effectuate a closure of tool assembly 304 and a firing of tool assembly 304 of loading unit 300.

As seen in FIG. 6, adapter 200 includes a pair of electrical contact pins 290a, 290b for electrical connection to a corresponding electrical plug 190a, 190b disposed in connecting portion 108a of surgical device 100. Electrical contacts 290a, 290b serve to allow for calibration and communication of life-cycle information to circuit board 150 of surgical device 100 via electrical plugs 190a, 190b that are electrically connected to circuit board 150. Adapter 200 further includes a circuit board supported in knob housing 202 and which is in electrical communication with electrical contact pins 290a, 290b.

When a button of surgical device is activated by the user, the software checks predefined conditions. If conditions are met, the software controls the motors and delivers mechanical drive to the attached surgical stapler, which can then open, close, rotate, articulate or fire depending on the function of the pressed button. The software also provides feedback to the user by turning colored lights on or off in a defined manner to indicate the status of surgical device 100, adapter 200 and/or loading unit 300.

Figure 26:
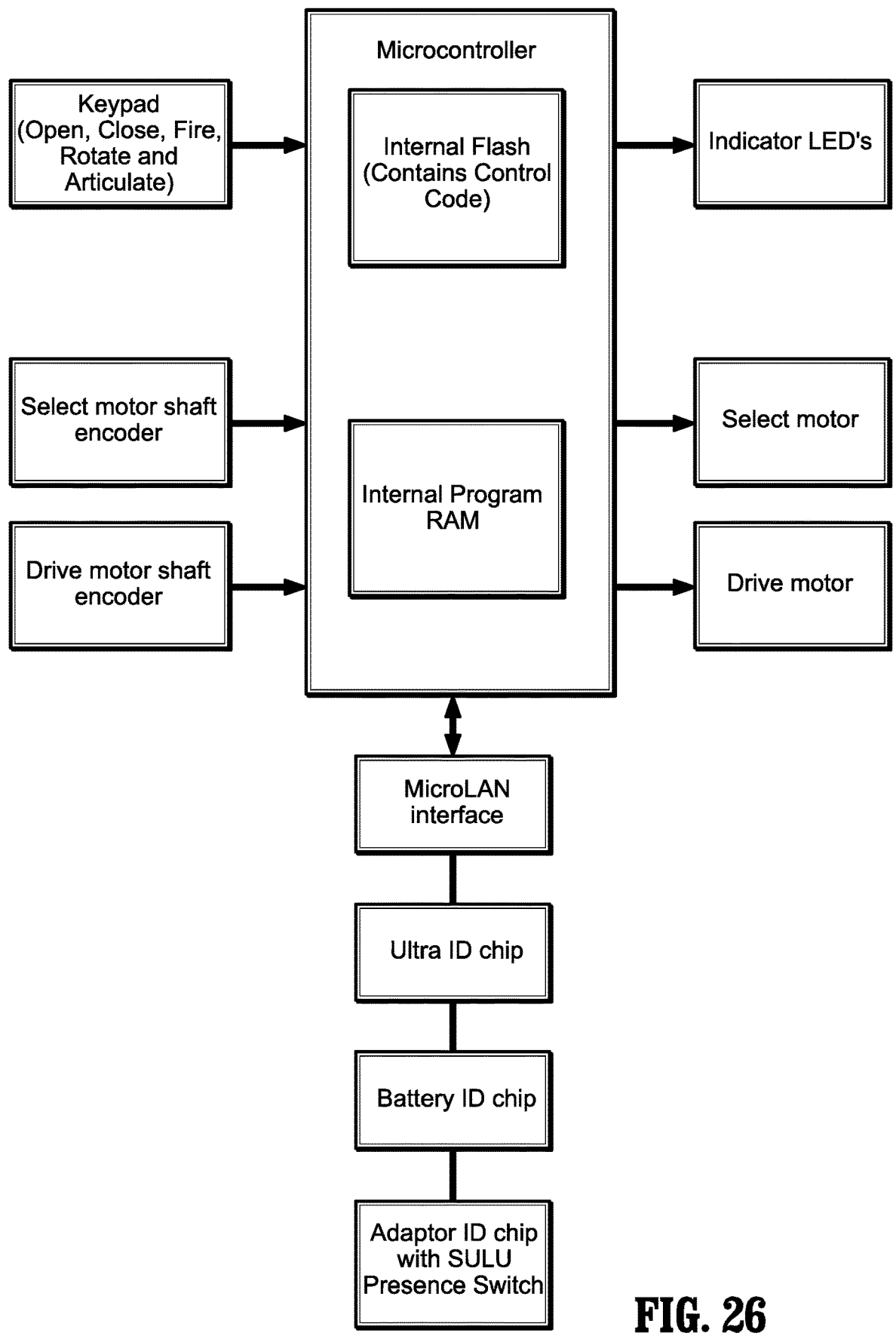
FIG. 26 is a schematic illustration of the outputs to the LEDs; selection of motor (to select clamping/cutting, rotation or articulation); and selection of the drive motors to perform a function selected.

A high level electrical architectural view of the system is shown in FIG. 26 and shows the connections to the various hardware and software interfaces. Inputs from presses of buttons 124, 126 and from motor encoders of the drive shaft are shown on the left side of FIG. 26. The microcontroller contains the device software that operates surgical device 100, adapter 200 and/or loading unit 300. The microcontroller receives inputs from and sends outputs to a MicroLAN, an Ultra ID chip, a Battery ID chip, and Adaptor ID chips. The MicroLAN, the Ultra ID chip, the Battery ID chip, and the Adaptor ID chips control surgical device 100, adapter 200 and/or loading unit 300 as follows:

| | |
|---|---|
| MicroLAN | Serial 1-wire bus communication to read/write system component ID information. |
| Ultra ID chip | identifies surgical device 100 and records usage information. |
| Battery ID chip | identifies the Battery 156 and records usage information. |
| Adaptor ID chip | identifies the type of adapter 200, records the presence of an end effector 300, and records usage information. |

The right side of the schematic illustrated in FIG. 26 indicates outputs to the LEDs; selection of motor (to select clamping/cutting, rotation or articulation); and selection of the drive motors to perform the function selected.

As illustrated in FIGS. 1 and 25, the loading unit is designated as 300. Loading unit 300 is configured and dimensioned for endoscopic insertion through a cannula, trocar or the like. In particular, in the embodiment illustrated in FIGS. 1 and 25, loading unit 300 may pass through a cannula or trocar when loading unit 300 is in a closed condition.

Loading unit 300 includes a proximal body portion 302 and a tool assembly 304. Proximal body portion 302 is releasably attached to a distal coupling 230 of adapter 200 and tool assembly 304 is pivotally attached to a distal end of proximal body portion 302. Tool assembly 304 includes an anvil assembly 306 and a cartridge assembly 308. Cartridge assembly 308 is pivotal in relation to anvil assembly 306 and is movable between an open or unclamped position and a closed or clamped position for insertion through a cannula of a trocar.

Proximal body portion 302 includes at least a drive assembly 360 and an articulation link 366.

Referring to FIG. 25, drive assembly 360 includes a flexible drive beam 364 having a distal end which is secured to a dynamic clamping member 365, and a proximal engagement section 368. Engagement section 368 includes a stepped portion defining a shoulder 370. A proximal end of engagement section 368 includes diametrically opposed inwardly extending fingers 372. Fingers 372 engage a hollow drive member 374 to fixedly secure drive member 374 to the proximal end of beam 364. Drive member 374 defines a proximal porthole 376 which receives connection member 247 of drive tube 246 of first drive converter assembly 240 of adapter 200 when loading unit 300 is attached to distal coupling 230 of adapter 200.

When drive assembly 360 is advanced distally within tool assembly 304, an upper beam of clamping member 365 moves within a channel defined between anvil plate 312 and anvil cover 310 and a lower beam moves over the exterior surface of carrier 316 to close tool assembly 304 and fire staples therefrom.

Proximal body portion 302 of loading unit 300 includes an articulation link 366 having a hooked proximal end 366a which extends from a proximal end of loading unit 300. Hooked proximal end 366a of articulation link 366 engages coupling hook 258c of drive bar 258 of adapter 200 when loading unit 300 is secured to distal housing 232 of adapter 200. When drive bar 258 of adapter 200 is advanced or retracted as described above, articulation link 366 of loading unit 300 is advanced or retracted within loading unit 300 to pivot tool assembly 304 in relation to a distal end of proximal body portion 302.

As illustrated in FIG. 25, cartridge assembly 308 of tool assembly 304 includes a staple cartridge 305 supportable in carrier 316. Staple cartridge 305 defines a central longitudinal slot 305a, and three linear rows of staple retention slots 305b positioned on each side of longitudinal slot 305a. Each of staple retention slots 305b receives a single staple 307 and a portion of a staple pusher 309. During operation of surgical device 100, drive assembly 360 abuts an actuation sled and pushes actuation sled through cartridge 305. As the actuation sled moves through cartridge 305, cam wedges of the actuation sled sequentially engage staple pushers 309 to move staple pushers 309 vertically within staple retention slots 305b and sequentially eject a single staple 307 therefrom for formation against anvil plate 312.

Reference may be made to U.S. Pat. No. 7,819,896 for a detailed discussion of the construction and operation of loading unit 300.

It will be understood that various modifications may be made to the embodiments of the presently disclosed adapter assemblies. For example, the battery 156 may be replaced with alternate sources of electrical power such as line voltage (either AC or DC) or a fuel cell. Therefore, the above description should not be construed as limiting, but merely as exemplifications of embodiments. Those skilled in the art will envision other modifications within the scope and spirit of the present disclosure.

What is claimed is:

1. An adapter assembly for selectively interconnecting a surgical loading unit and a handle assembly, the adapter assembly comprising:
   a drive coupling assembly including:
      a first drive element configured to couple to a first drive connector of the handle assembly;
      a second drive element configured to couple to a second drive connector of the handle assembly; and
      a third drive element configured to couple to a third drive connector of the handle assembly; and
   a knob housing coupled to the drive coupling assembly and defining a central longitudinal axis, wherein the first drive element is disposed on the central longitudinal axis and offset from a plane cooperatively defined by the second and third drive elements, each of the first, second, and third drive elements being configured to rotate relative to the knob housing, the third drive element being offset from the second drive element.

2. The adapter assembly according to claim 1, wherein the drive coupling assembly extends proximally from a proximal end portion of the knob housing.

3. The adapter assembly according to claim 1, further comprising:
   a drive nut threadably engaged with a distal portion of the first drive element; and
   a distal drive member having a proximal portion disposed in mechanical cooperation with a distal portion of the drive nut.

4. The adapter assembly according to claim 3, wherein the distal portion of the first drive element includes external threading, and the drive nut is elongated and has an internal threaded portion mechanically engaged to the external threading of the distal portion of the first drive element.

5. The adapter assembly according to claim 3, wherein the distal drive member is configured to translate without rotating in response to a rotation of the first drive element.

6. The adapter assembly according to claim 3, wherein each of the drive nut and the distal drive member is coaxial with the central longitudinal axis of the knob housing.

7. The adapter assembly according to claim 3, wherein the first drive element defines a longitudinal axis between proximal and distal ends thereof, and wherein a radial center of each of the first drive element, the drive nut, and the distal drive member is disposed on the longitudinal axis of the drive element.

8. The adapter assembly according to claim 3, further comprising a pair of thrust bearings disposed about the first drive element and proximally of the drive nut.

9. The adapter assembly according to claim 3, further comprising a linking assembly mechanically coupling the proximal portion of the distal drive member and the distal portion of the drive nut.

10. The adapter assembly according to claim 9, wherein the linking assembly includes a first pin and a second pin, the first and second pins being disposed perpendicularly to the central longitudinal axis of the knob housing and extending partially through the proximal portion of the distal drive member and the distal portion of the drive nut.

11. The adapter assembly according to claim 1, wherein the second and third drive elements are radially off-center with respect to the central longitudinal axis of the knob housing.

12. The adapter assembly according to claim 1, further comprising an outer tube extending from a distal portion of the knob housing.

13. The adapter assembly according to claim 12, further comprising a loading unit coupling assembly disposed on a distal portion of the outer tube.

14. The adapter assembly according to claim 1, wherein the drive coupling assembly further includes first, second, and third connector sleeves keyed to the first, second, and third drive elements, respectively, such that rotation of each of the first, second, and third connector sleeves causes independent rotation of the first, second, and third drive elements, respectively.

15. The adapter assembly according to claim 1, wherein the drive coupling assembly defines a central longitudinal axis that is radially off-center from the central longitudinal axis of the knob housing.

16. The adapter assembly according to claim 1, wherein the second and third drive elements are disposed on opposite sides of the first drive element.

17. The adapter assembly according to claim 1, wherein the drive coupling assembly further includes a drive coupling housing extending proximally from the knob housing, each of the first, second, and third drive elements being rotatably supported in the drive coupling housing.

18. The adapter assembly according to claim 17, wherein the drive coupling housing defines a central longitudinal axis that is offset from the central longitudinal axis of the knob housing.

19. The adapter assembly according to claim 18, wherein the central longitudinal axis of the drive coupling housing extends between the second and third drive elements and is on the plane cooperatively defined by the second and third drive elements.

20. An adapter assembly for selectively interconnecting a surgical loading unit and a handle assembly, the adapter assembly comprising:
   a drive coupling assembly including:
      a first drive element configured to couple to a first drive connector of the handle assembly;
      a second drive element configured to couple to a second drive connector of the handle assembly; and
      a third drive element configured to couple to a third drive connector of the handle assembly;
   a knob housing coupled to the drive coupling assembly and defining a central longitudinal axis, wherein the first drive element is disposed on the central longitudinal axis and offset from a plane cooperatively defined by the second and third drive elements;

a drive nut threadably engaged with a distal portion of the first drive element;
a distal drive member having a proximal portion disposed in mechanical cooperation with a distal portion of the drive nut; and
a linking assembly mechanically coupling the proximal portion of the distal drive member and the distal portion of the drive nut, wherein the linking assembly includes a first pin and a second pin, the first and second pins being disposed perpendicularly to the central longitudinal axis of the knob housing and extending partially through the proximal portion of the distal drive member and the distal portion of the drive nut.

* * * * *